(12) United States Patent
Lifshitz-Liron et al.

(10) Patent No.: US 7,563,918 B2
(45) Date of Patent: Jul. 21, 2009

(54) SOLID AND CRYSTALLINE IBANDRONATE SODIUM AND PROCESSES FOR PREPARATION THEREOF

(75) Inventors: Revital Lifshitz-Liron, Herzlia (IL); Thomas Bayer, Tel Aviv (IL); Judith Aronhime, Rehovot (IL); Michael Pinchasov, Dover, NJ (US)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 221 days.

(21) Appl. No.: 11/644,568

(22) Filed: Dec. 22, 2006

(65) Prior Publication Data

US 2007/0179119 A1      Aug. 2, 2007

Related U.S. Application Data

(63) Continuation of application No. 11/410,825, filed on Apr. 24, 2006, now abandoned, which is a continuation of application No. 11/211,062, filed on Aug. 23, 2005, now abandoned.

(60) Provisional application No. 60/604,026, filed on Aug. 23, 2004, provisional application No. 60/690,867, filed on Jun. 16, 2005.

(51) Int. Cl.
*C07C 229/00* (2006.01)
(52) U.S. Cl. ...................... 558/155; 558/156
(58) Field of Classification Search ............ 558/155, 558/156
See application file for complete search history.

(56) References Cited

U.S. PATENT DOCUMENTS

| | | | |
|---|---|---|---|
| 4,927,814 A | 5/1990 | Gall et al. | |
| 6,294,196 B1 * | 9/2001 | Gabel et al. | 424/464 |
| 2006/0172975 A1 | 8/2006 | Eiermann et al. | |
| 2006/0172976 A1 | 8/2006 | Eiermann et al. | |

FOREIGN PATENT DOCUMENTS

| WO | WO03/093282 | 1/2003 |
|---|---|---|
| WO | WO 2005/063779 | 7/2005 |
| WO | WO 2006/002348 | 1/2006 |
| WO | WO2007/074475 | 7/2007 |

OTHER PUBLICATIONS

Ansel et al., Pharmaceutical Dosage Forms and Drug Delivery Systems, (7th ed. 1999), table of contents.
Brittain, et al., Polymorphism in Pharmaceutical Solids, Drugs and the Pharmaceutical Sciences, vol. 95 (Marcel Dekker, Inc. New York 1999), table of contents.
Caira, M.R., et al. "Crystalline Polymorphism of Organic Compounds", Topics in Current Chemistry, 198: 163-208 (1998).
Craig, D.Q.M., et al., "The relevance of the amorphous state to pharmaceutical dosage forms: Glassy drugs and freeze dried systems", International Journal of Pharmaceutics, 179(2): 179-207 (1999).
Gennaro, A.R., Remington: The Science and Practice of Pharmacy, pp. 681-699 (20th ed. 2000).
Hancock B.C., et al., "Characteristics and Significance of the Amorphous State in Pharmaceutical Systems", Journal of Pharmaceutical Sciences, 86(1): 1-12 (1997).
Monier-Faugere M-C, et al., "A new Bisphosphonate, BM 21.0955, Prevents Bone Loss Associated with Cessation of Ovarian Function in Experimental Dogs", Journal of Bone and Mineral Research, 8(11): 1345-1355 (1993).
Dallas, Sarah L., et al., "Ibandronate Reduces Osteolytic Lesions but not Tumor Burden in a Murine Model of Myeloma Bone Disease", Blood, 1999, pp. 1697-1706.
Third Party Observation Cited on Jan. 14, 2009 in European Counterpart Application No. 05791142.2 and Publication No. EP 1 713 489.
Third Party Observation Cited on Feb. 4, 2009 in European Counterpart Application No. 05791142.2 and Publication No. EP 1 713 489.
United States Food and Drug Administration, Center for Drug Evaluation and Research, Application No. 21-455 "Chemistry Review(s)" for Boniva Tablets, 2.5 mg, Approved May 16, 2003.

* cited by examiner

*Primary Examiner*—Rei-tsang Shiao
(74) *Attorney, Agent, or Firm*—Kenyon & Kenyon LLP

(57) ABSTRACT

The present invention relates to solid amorphous and crystalline forms of ibandronate sodium.

9 Claims, 13 Drawing Sheets

X-Ray powder diffractogram of Form C Ibandronate Sodium

X-Ray powder diffractogram of Form D Ibandronate Sodium

X-Ray powder diffractogram of Form E Ibandronate Sodium

X-Ray powder diffractogram of Form F Ibandronate Sodium

X-Ray powder diffractogram of Form G Ibandronate Sodium

X-Ray powder diffractogram of Form H Ibandronate Sodium

X-Ray powder diffractogram of Form J Ibandronate Sodium

X-Ray powder diffractogram of Form K Ibandronate Sodium

X-Ray powder diffractogram of Form K2 Ibandronate Sodium

X-Ray powder diffractogram of Form K3 Ibandronate Sodium

X-Ray powder diffractogram of Form Q Ibandronate Sodium

X-Ray powder diffractogram of Form Q1 Ibandronate Sodium

X-Ray powder diffractogram of Form Q1 Ibandronate Sodium

X-Ray powder diffractogram of Form Q2 Ibandronate Sodium

X-Ray powder diffractogram of Form Q2 Ibandronate Sodium

X-Ray powder diffractogram of Form Q3 Ibandronate Sodium

X-Ray powder diffractogram of Form Q4 Ibandronate Sodium

X-Ray powder diffractogram of Form Q5 Ibandronate Sodium

X-Ray powder diffractogram of Form Q6 Ibandronate Sodium

X-Ray powder diffractogram of Form QQ Ibandronate Sodium

X-Ray powder diffractogram of Form R Ibandronate Sodium

X-Ray powder diffractogram of Form S Ibandronate Sodium

X-Ray powder diffractogram of Form S Ibandronate Sodium

X-Ray powder diffractogram of Form T Ibandronate Sodium

X-Ray powder diffractogram of amorphous Ibandronate Sodium

SOLID AND CRYSTALLINE IBANDRONATE SODIUM AND PROCESSES FOR PREPARATION THEREOF

This application is a continuation of U.S. patent application Ser. No. 11/410,825 filed Apr. 24, 2006 now abandoned which is a continuation of U.S. patent application Ser. No. 11/211,062 filed Aug. 23, 2005 now abandoned and claims the benefit of U.S. Provisional Patent Application Ser. No. 60/604,026 filed Aug. 23, 2004 and Provisional Application Ser No. 60/690,867, filed Jun. 16, 2005.

FIELD OF THE INVENTION

The present invention relates to the solid state chemistry of Ibandronate sodium.

BACKGROUND OF THE INVENTION

The empirical formula for ibandronate sodium is $C_9H_{22}NO_7P_2Na \cdot H_2O$. The chemical name of ibandronate sodium is (1-hydroxy-3-(N-methyl-N-pentylamino)propylidene) bisphosphonic acid monosodium salt. The chemical structure of ibandronate sodium is the following:

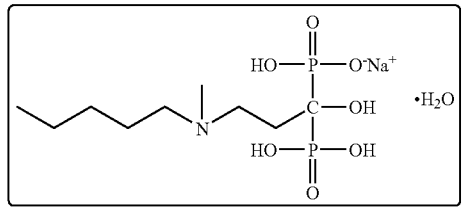

The chemical structure of ibandronic acid (IBD-Ac) is the following:

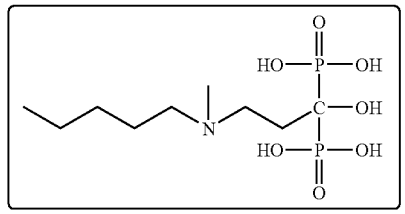

Ibandronate sodium is a third-generation nitrogen-containing bisphosphonate characterized by an aliphatic tertiary amine side chain. Ibandronate sodium is a white powder.

U.S. Pat. No. 4,972,814 discloses diphosphonic acid derivatives, processes for the preparation thereof, and pharmaceutical compositions containing them.

Boniva® (ibandronate sodium) was developed by Hoffmann-La Roche for the treatment of bone disorders such as hypercalcaemia of malignancy, osteolysis, Paget's disease, osteoporosis, and metastatic bone disease. It is available as an intravenous injection administered every 2-3 months and as an oral formulation.

Boniva® is also marketed in Europe under the name Bondronat® for cancer-related bone complications. Bondronat® is available in ampoule with 1 ml concentrate for solution for infusion contains 1.125 mg of ibandronic monosodium salt monohydrate, corresponding to 1 mg of ibandronic acid.

The present invention relates to the solid state physical properties of ibandronate sodium. These properties can be influenced by controlling the conditions under which ibandronate sodium is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must necessitate the use of glidants such as colloidal silicon dioxide, talc, starch, or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulation syrups, elixirs, and other liquid medicaments. The solid state form of a compound can also affect its behavior on compaction and its storage stability.

These practical physical characteristics are influenced by the conformation and orientation of molecules in the unit cell, which define a particular polymorphic form of a substance. The polymorphic form can give rise to thermal behavior different from that of the amorphous material or another polymorphic form. Thermal behavior is measured in the laboratory by such techniques as capillary melting point, thermogravimetric analysis (TGA), and differential scanning calorimetry (DSC) and can be used to distinguish some polymorphic forms from others. A particular polymorphic form can also give rise to distinct spectroscopic properties that can be detectable by powder x-ray crystallography, solid state $^{13}C$ NMR spectrometry, and infrared spectrometry.

Generally, the crystalline solid has improved chemical and physical stability over the amorphous form, and forms with low crystallinity. They can also exhibit improved solubility, hygroscopicity, bulk properties, and/or flowability.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. There is a need in the art for additional polymorphic forms of ibandronate sodium.

SUMMARY OF THE INVENTION

In one aspect, the present invention provides new crystalline forms of ibandronate sodium, an amorphous form of ibandronate sodium, and processes for preparing these forms.

In another aspect, the present invention provides solid crystalline ibandronate sodium solvate.

In another aspect, the present invention provides solid crystalline ibandronate sodium alcoholate.

In another aspect, the present invention provides solid crystalline ibandronate sodium ethanolate.

In another aspect, the present invention provides solid crystalline ibandronate sodium butanolate.

In another aspect, the present invention provides solid crystalline ibandronate sodium denominated Form C, characterized by x-ray powder diffraction reflections at 4.7, 5.0, 17.2, 18.3 and 19.5±0.2 degrees two-theta. Form C can exist as a monoethanolate.

In another aspect, the present invention provides solid crystalline ibandronate sodium denominated Form D, characterized by x-ray powder diffraction reflections at 4.8, 9.3, 18.5, 23.1, and 36.1±0.2 degrees two-theta.

In another aspect, the present invention provides solid crystalline ibandronate sodium denominated Form E, characterized by x-ray powder diffraction reflections at 4.6, 4.8, 5.3, 9.3, and 34.7±0.2 degrees two-theta. Form E can exist as a hemibutanolate.

In another aspect, the present invention provides solid crystalline ibandronate sodium denominated Form F, characterized by x-ray powder diffraction reflections at 4.9, 5.1, 6.0, 20.0, and 36.4±0.2 degrees two-theta.

In another aspect, the present invention provides solid crystalline ibandronate sodium denominated Form G, characterized by x-ray powder diffraction reflections at 4.7, 9.2, 17.4, 18.4, and 19.9±0.2 degrees two-theta.

In another aspect, the present invention provides solid crystalline ibandronate sodium denominated Form H, characterized by x-ray powder diffraction reflections at 4.8, 5.7, 17.3, 19.5, and 26.0±0.2 degrees two-theta.

In another aspect, the present invention provides solid crystalline ibandronate sodium denominated Form J, characterized by x-ray powder diffraction reflections at 4.6, 9.2, 18.3, 19.6, and 25.6±0.2 degrees two-theta.

In another aspect, the present invention provides solid crystalline ibandronate sodium denominated Form K, characterized by x-ray powder diffraction reflections at 5.0, 5.9, 17.2, 20.0, and 25.9±0.2 degrees two-theta.

In another aspect, the present invention provides solid crystalline ibandronate sodium denominated form K2, characterized by x-ray powder diffraction reflections at 5.1, 6.1, 17.3, 20.1, and 21.5±0.2 degrees two-theta.

In another aspect, the present invention provides solid crystalline ibandronate sodium denominated Form K3, characterized by x-ray powder diffraction reflections at 5.1, 6.2, 17.3, 19.7, and 20.1±0.2 degrees two-theta.

In another aspect, the present invention provides solid crystalline ibandronate sodium denominated Form Q, characterized by x-ray powder diffraction reflections at 5.0, 6.1, 17.2, 25.7, and 30.9±0.2 degrees two-theta.

In another aspect, the present invention provides solid crystalline ibandronate sodium denominated Form Q1, characterized by x-ray powder diffraction reflections at 4.7, 6.0, 17.2, 26.2, and 31.0±0.2 degrees two-theta.

In another aspect, the present invention provides solid crystalline ibandronate sodium denominated Form Q2, characterized by x-ray powder diffraction reflections at 4.9, 6.2, 25.9, 31.0, and 37.1±0.2 degrees two-theta.

In another aspect, the present invention provides solid crystalline ibandronate sodium denominated Form Q3, characterized by x-ray powder diffraction reflections at 5.9, 17.1, 19.6, 20.2, and 21.3±0.2 degrees two-theta.

In another aspect, the present invention provides solid crystalline ibandronate sodium denominated Form Q4, characterized by x-ray powder diffraction reflections at 6.1, 17.2, 19.6, 20.3, and 21.4±0.2 degrees two-theta.

In another aspect, the present invention provides solid crystalline ibandronate sodium denominated Form Q5, characterized by x-ray powder diffraction reflections at 6.1, 17.2, 19.6, 20.1, and 21.5±0.2 degrees two-theta.

In another aspect, the present invention provides is solid crystalline ibandronate sodium denominated Form Q6, characterized by x-ray powder diffraction reflections at 6.1, 17.3, 19.6, 21.5, and 30.8±0.2 degrees two-theta.

In another aspect, the present invention provides solid crystalline ibandronate sodium denominated Form QQ, characterized by x-ray powder diffraction reflections at 6.2, 25.9, 26.7, 31.1, and 37.2±0.2 degrees two-theta.

In another aspect, the present invention provides solid crystalline ibandronate sodium denominated Form R, characterized by x-ray powder diffraction reflections at 5.3, 6.0, 17.2, 18.7, and 20.0±0.2 degrees two-theta. Form R can exist as a hemiethanolate.

In another aspect, the present invention provides solid crystalline ibandronate sodium denominated Form S, characterized by x-ray powder diffraction reflections at 4.8, 5.1, 5.3, 5.4, and 6.1±0.2 degrees two-theta. Form S can exist as a hemiethanolate.

In another aspect, the present invention provides solid crystalline ibandronate sodium denominated Form T, characterized by x-ray powder diffraction reflections at 6.2, 15.7, 26.3, 32.6, and 35.6±0.2 degrees two-theta.

In yet another aspect, the present invention provides solid amorphous ibandronate sodium.

DETAILED DESCRIPTION OF THE INVENTION

The present invention provides new crystalline forms of ibandronate sodium, as well as an amorphous form of ibandronate sodium. In one embodiment, the present invention provides each crystalline form substantially free from other crystalline forms, i.e., containing no more than about 5% of another crystalline forms. The present invention also provides processes for preparing each described solid form of ibandronate sodium.

The present invention also provides solvate forms of ibandronate sodium. The range of solvent content for such solvates is defined below:

| Solvate Form | Range of Solvent Content (by weight) |
| --- | --- |
| 1/3 ethanolate: | 4-5% |
| monoethanolate: | 8-12% |
| hemibutanolate | 8-10% |

The present invention provides solid crystalline ibandronate sodium alcoholates.

The present invention provides solid crystalline ibandronate sodium ethanolate. The present invention also provides solid crystalline ibandronate sodium monoethanolate and hemiethanolate.

The present invention further provides solid crystalline ibandronate sodium butanolate. The present invention also provides solid crystalline ibandronate sodium hemibutanolate.

Figure 1:
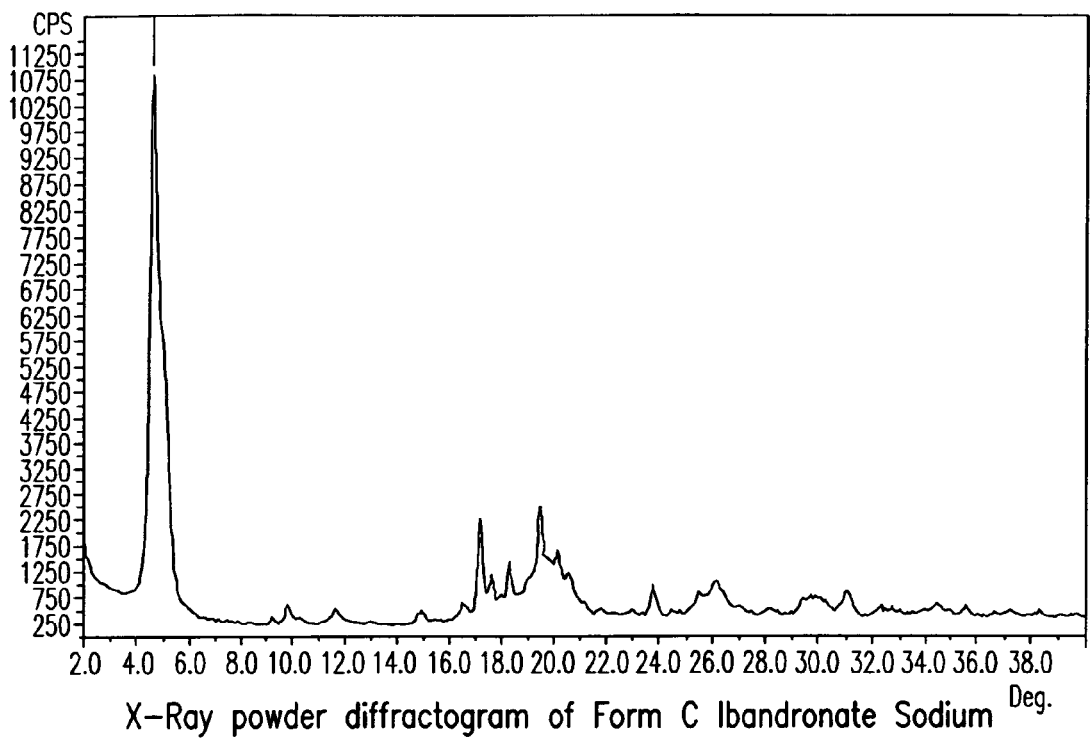
FIG. 1 is an x-ray powder diffractogram of ibandronate sodium Form C.

In one embodiment, the present invention provides a solid crystalline form of ibandronate sodium denominated Form C. Form C is characterized by x-ray powder diffraction reflections at 4.7, 5.0, 17.2, 18.3, and 19.5±0.2 degrees two-theta. Form C can be further characterized by x-ray powder diffraction reflections at 17.6, 19.7, 20.2, 20.6, and 23.8±0.2 degrees two-theta. FIG. 1 shows a representative powder x-ray diffraction diagram for Form C. Form C can be a monohydrate and/or monoethanolate. Form C can be further characterized by TGA, showing a weight loss of about 15 to about 16%.

Figure 2:
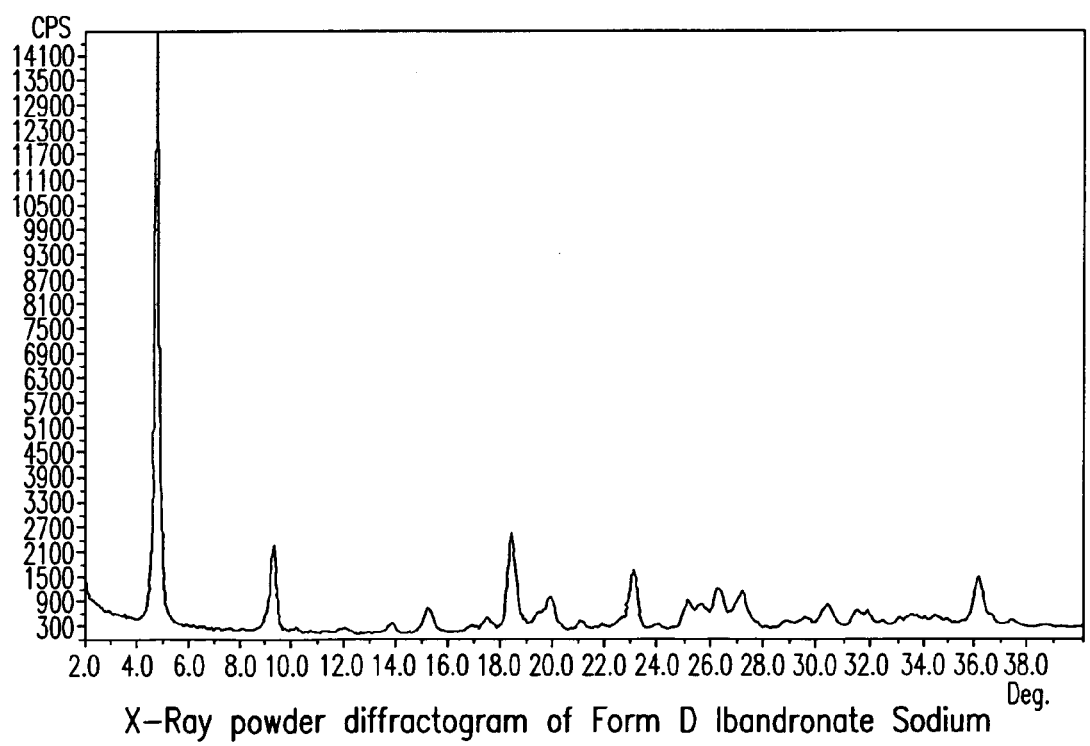
FIG. 2 is an x-ray powder diffractogram of ibandronate sodium Form D.

In another embodiment, the present invention provides a solid crystalline form of ibandronate sodium denominated Form D. Form D is characterized by x-ray powder diffraction reflections at 4.8, 9.3, 18.5, 23.1, and 36.1±0.2 degrees two-theta, Form D can be further characterized by x-ray powder diffraction reflections at 15.3, 19.9, 26.3, 27.2, and 30.4±0.2 degrees two-theta. FIG. 2 shows a representative powder x-ray diffraction diagram for Form D. Form D can be a hexahydrate. Form D can be further characterized by TGA, showing a weight loss of about 24 to about 26%.

Figure 3:
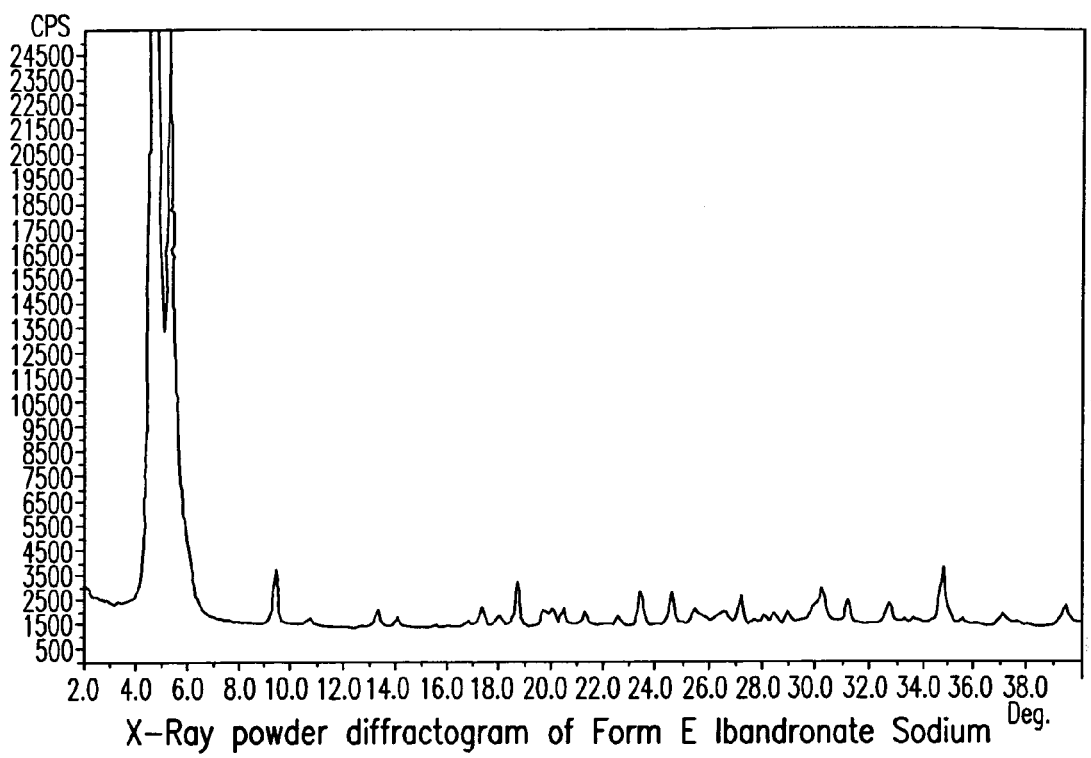
FIG. 3 is an x-ray powder diffractogram of ibandronate sodium Form E.

In another embodiment, the present invention provides a solid crystalline form of ibandronate sodium denominated Form E. Form E is characterized by x-ray powder diffraction reflections at 4.6, 4.8, 5.3, 9.3, and 34.7±0.2 degrees two-theta. Form E can be further characterized by x-ray powder diffraction reflections at 18.6, 23.3, 24.5, 27.1, and 30.1±0.2 degrees two-theta. FIG. 3 shows a representative powder x-ray diffraction diagram for Form E. Form E can be a hemibutanolate and/or a sesquihydrate. Form E can be further characterized by TGA, showing a weight loss of about 14 to about 21%.

Figure 4:
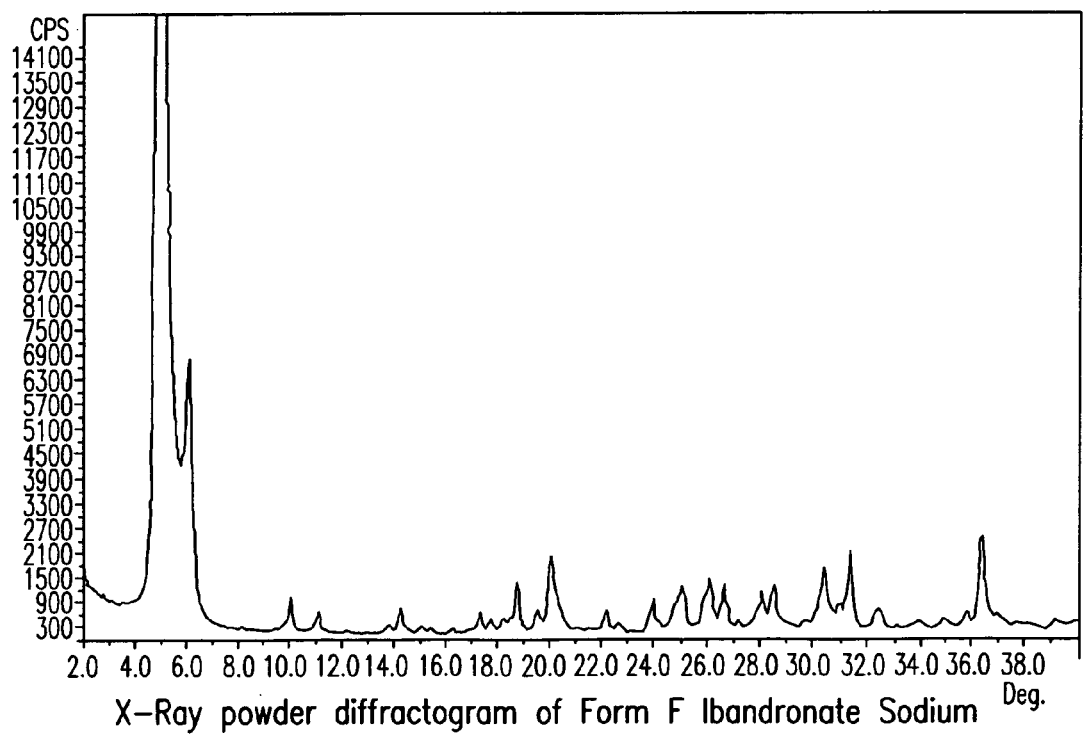
FIG. 4 is an x-ray powder diffractogram of ibandronate sodium Form F.

In another embodiment, the present invention provides a solid crystalline form of ibandronate sodium denominated Form F. Form F is characterized by x-ray powder diffraction reflections at 4.9, 5.1, 6.0, 20.0, and 36.4±0.2 degrees two-theta. Form F can be further characterized by x-ray powder diffraction reflections at 18.6, 26.0, 28.5, 30.4, and 31.3±0.2 degrees two-theta. FIG. 4 shows a representative powder x-ray diffraction diagram for Form F. Form F can be further characterized by TGA, showing a weight loss of about 10 to about 32%.

Figure 5:
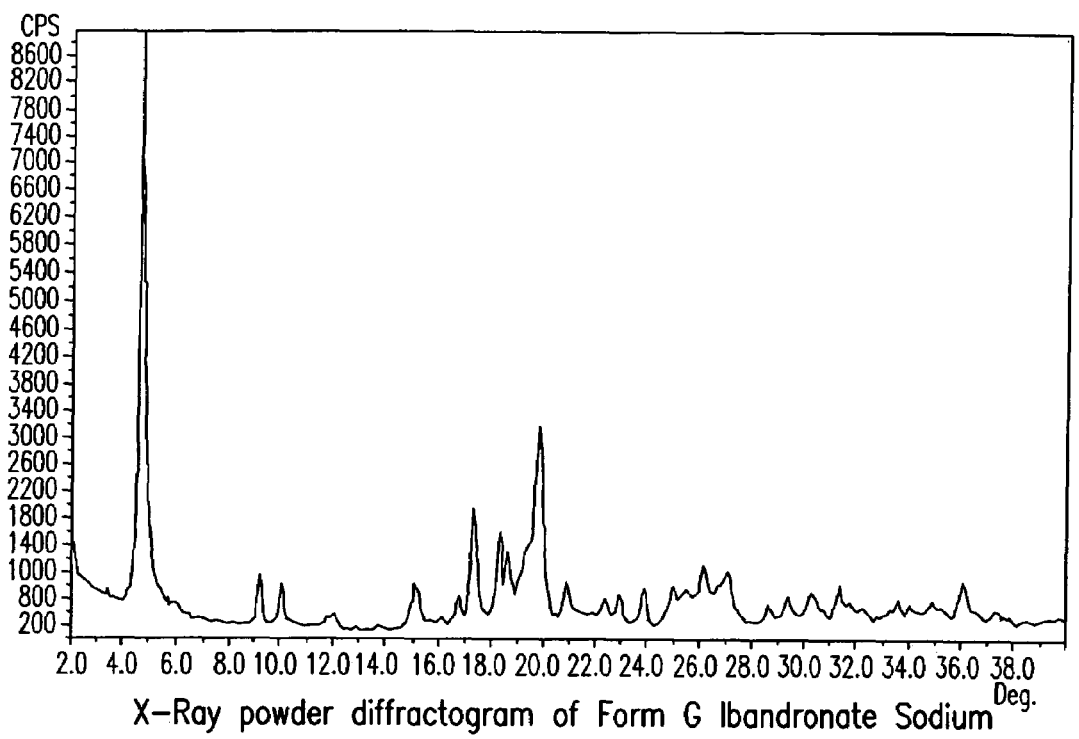
FIG. 5 is an x-ray powder diffractogram of ibandronate sodium Form G.

In another embodiment, the present invention provides a solid crystalline form of ibandronate sodium denominated Form G. Form G is characterized by x-ray powder diffraction reflections at 4.7, 9.2, 17.4, 18.4, and 19.9±0.2 degrees two-theta. Form G can be further characterized by x-ray powder diffraction reflections at 10.1, 15.2, 18.7, 26.3, and 27.1±0.2 degrees two-theta. FIG. 5 shows a representative powder x-ray diffraction diagram for Form G. Form G can be a hexahydrate. Form G can be further characterized by TGA, showing a weight loss of about 22 to about 25%.

Figure 6:
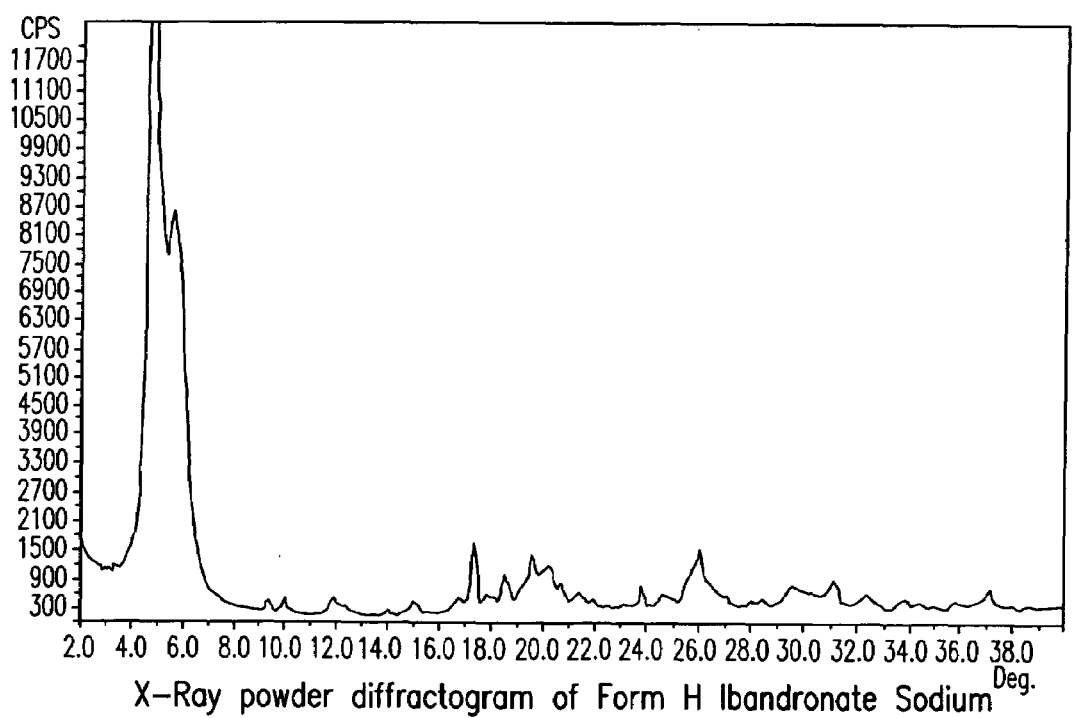
FIG. 6 is an x-ray powder diffractogram of ibandronate sodium Form H.

In another embodiment, the present invention provides a solid crystalline form of ibandronate sodium denominated Form H. Form H is characterized by x-ray powder diffraction reflections at 4.8, 5.7, 17.3, 19.5, and 26.0±0.2 degrees two-theta. Ibandronate sodium Form H can be further characterized by x-ray powder diffraction reflections at 18.5, 20.1, 23.8, 31.1, and 37.1±0.2 degrees two-theta. FIG. 6 shows a representative powder x-ray diffraction diagram for Form H. Form H can be further characterized by TGA, showing a weight loss of about 13 to about 16%.

Figure 7:
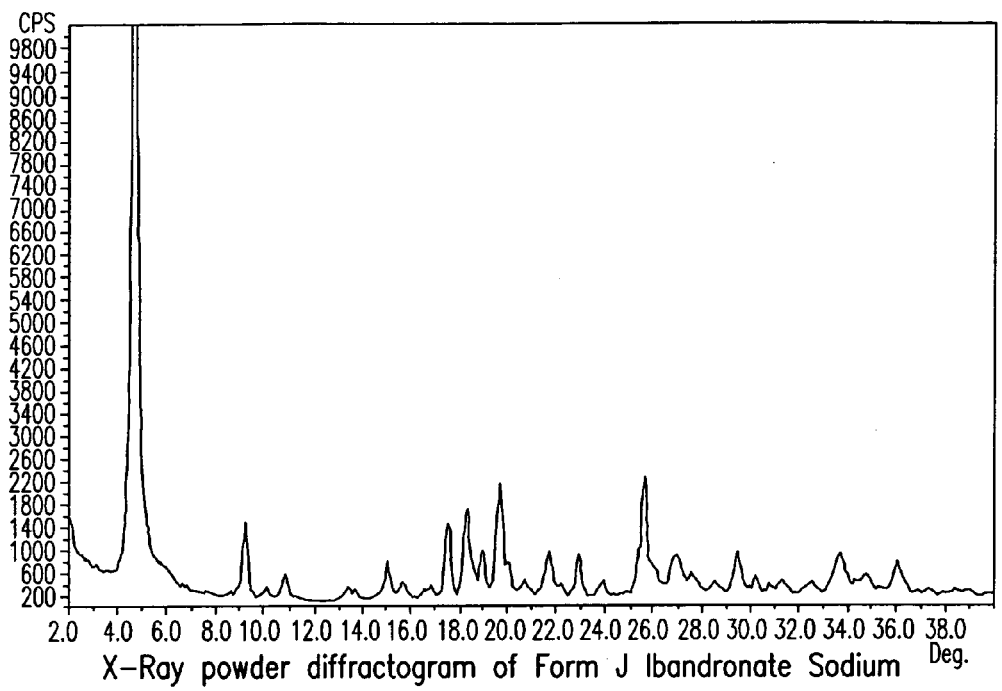
FIG. 7 is an x-ray powder diffractogram of ibandronate sodium Form J.

In another embodiment, the present invention provides a solid crystalline form of ibandronate sodium denominated Form J. Form J is characterized by x-ray powder diffraction reflections at 4.6, 9.2, 18.3, 19.6, and 25.6±0.2 degrees two-theta. Form J can be further characterized by x-ray powder diffraction reflections at 17.5, 18.9, 21.7, 22.9, and 29.5±0.2 degrees two-theta. FIG. 7 shows a representative powder x-ray diffraction diagram for Form J. Form J can be a hexahydrate. Form J can be further characterized by TGA, showing a weight loss of about 22 to about 23%.

Figure 8:
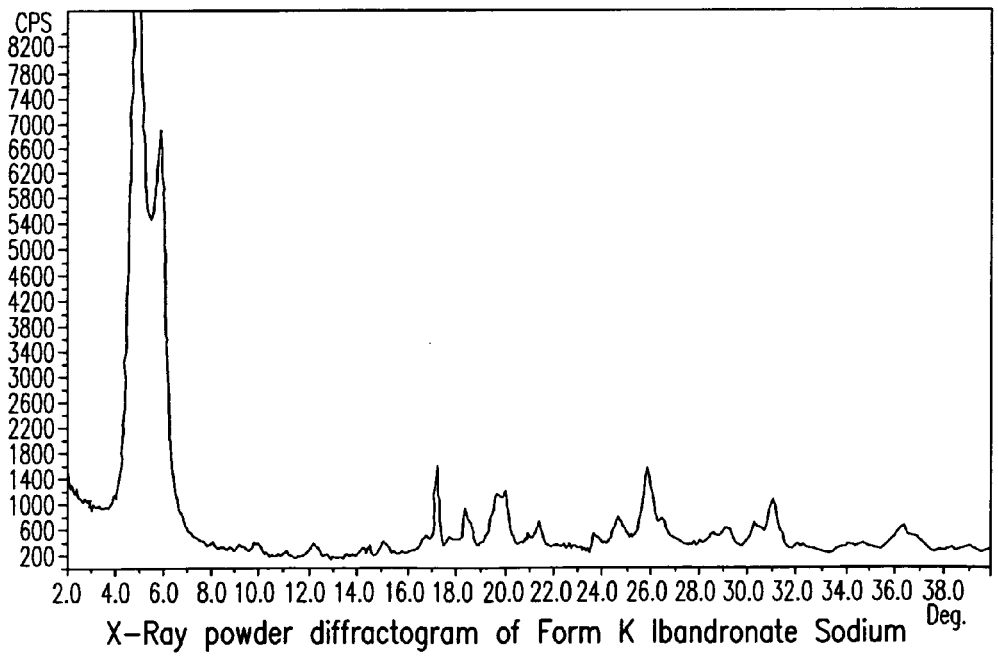
FIG. 8 is an x-ray powder diffractogram of ibandronate sodium Form K.

In another embodiment, the present invention provides a solid crystalline form of ibandronate sodium denominated Form K. Form K is characterized by x-ray powder diffraction reflections at 5.0, 5.9, 17.2, 20.0, and 25.9±0.2 degrees two-theta. Form K can be further characterized by x-ray powder diffraction reflections at 18.5, 19.7, 21.4, 26.5, and 31.1±0.2 degrees two-theta. FIG. 8 shows a representative powder x-ray diffraction diagram for Form K. Form K can be a sesquihydrate. Form K can be further characterized by TGA, showing a weight loss of about 10 to about 15%.

Figure 9:
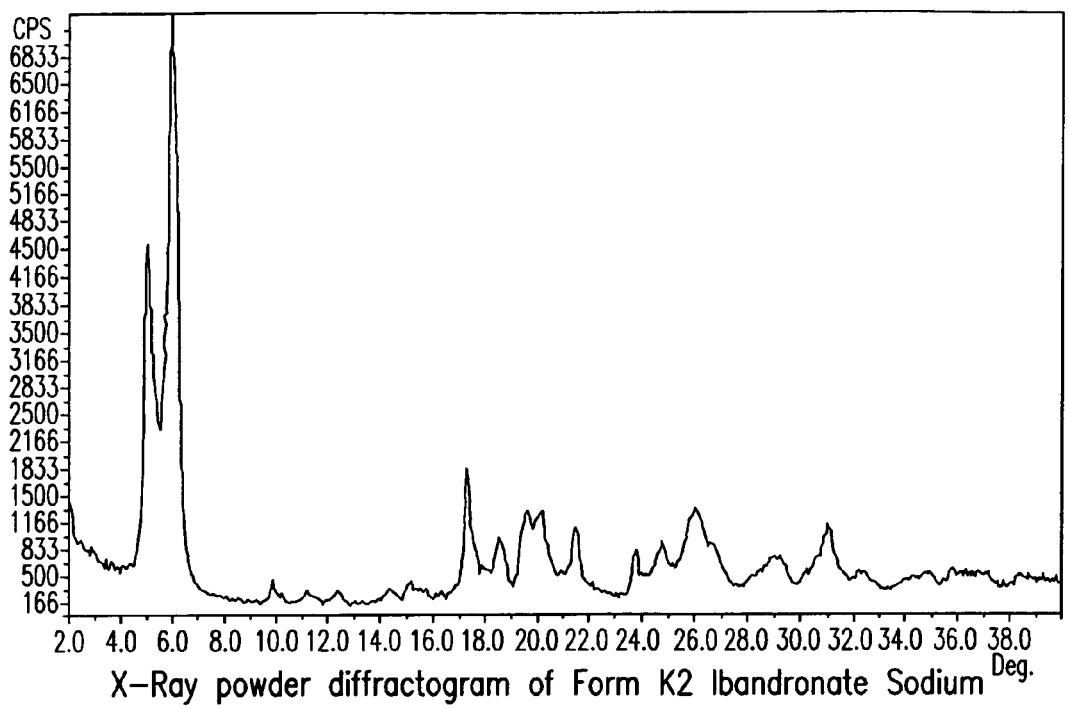
FIG. 9 is an x-ray powder diffractogram of ibandronate sodium Form K2.

In another embodiment, the present invention provides a solid crystalline form of ibandronate sodium denominated Form K2. Form K2 is characterized by x-ray powder diffraction reflections at 5.1, 6.1, 17.3, 20.1, and 21.5±0.2 degrees two-theta. Form K2 can be further characterized by x-ray powder diffraction reflections at 18.6, 19.6, 26.1, 26.8, and 31.1±0.2 degrees two-theta. FIG. 9 shows a representative powder x-ray diffraction diagram for Form K2. Form K2 can be further characterized by TGA, showing a weight loss of about 9 to about 10%.

Figure 10:
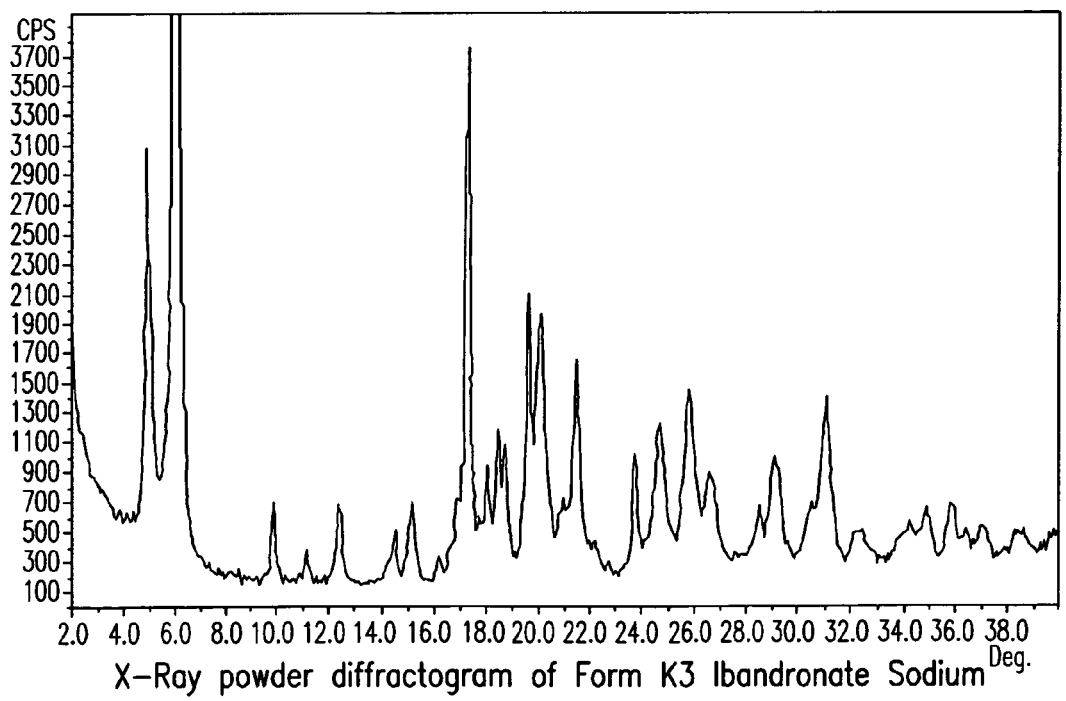
FIG. 10 is an x-ray powder diffractogram of ibandronate sodium Form K3.

In another embodiment, the present invention provides a solid crystalline form of ibandronate sodium denominated Form K3. Form K3 is characterized by x-ray powder diffraction reflections at 5.1, 6.2, 17.3, 19.7, and 20.1±0.2 degrees two-theta. Form K3 can be further characterized by x-ray powder diffraction reflections at 18.5, 21.5, 23.8, 25.8, and 31.1±0.2 degrees two-theta. FIG. 10 shows a representative powder x-ray diffraction diagram for Form K3. Form K3 can be further characterized by TGA, showing a weight loss of about 7 to about 8%.

Figure 11:
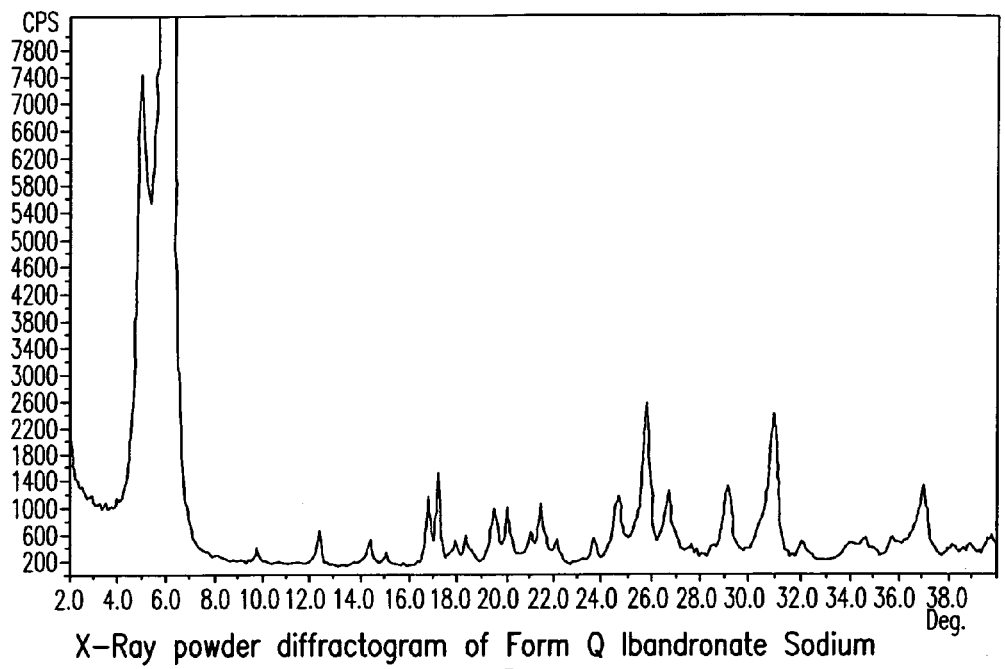
FIG. 11 is an x-ray powder diffractogram of ibandronate sodium Form Q.

In another embodiment, the present invention provides a solid crystalline form of ibandronate sodium denominated Form Q. Form Q is characterized by x-ray powder diffraction reflections at 5.0, 6.1, 17.2, 25.7, and 30.9±0.2 degrees two-theta. Form Q can be further characterized by x-ray powder diffraction reflections at 16.8, 21.4, 26.7, 29.1, and 36.9±0.2 degrees two-theta. FIG. 11 shows a representative powder x-ray diffraction diagram for Form Q. Form Q can be in the range of a monohydrate to a hexahydrate. Form Q can be further characterized by TGA, showing a weight loss of about 5 to about 25%.

Figure 12:
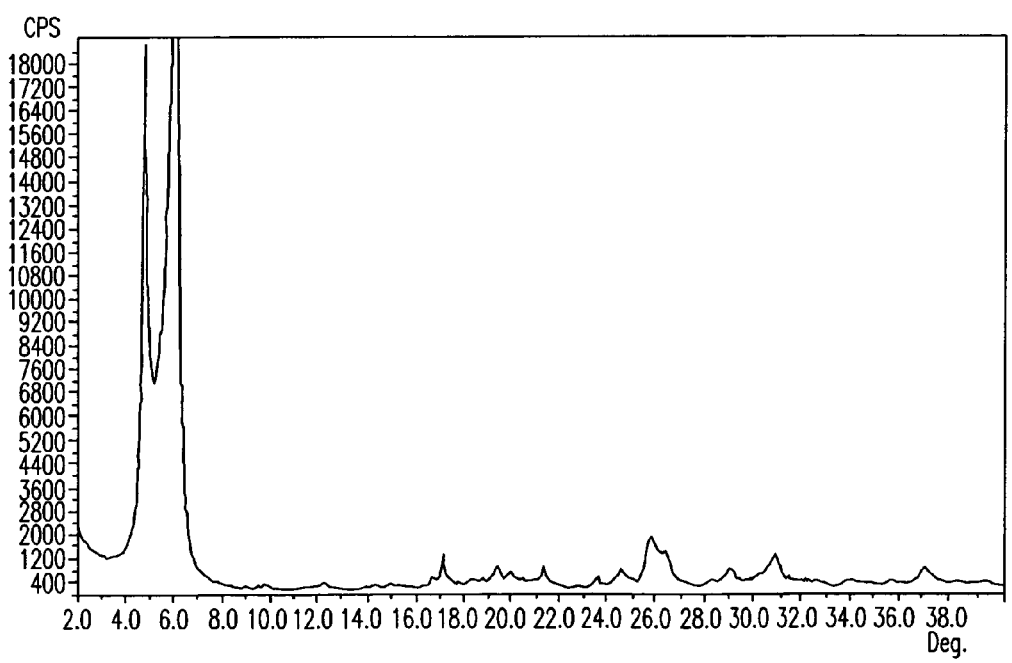
FIG. 12 is an x-ray powder diffractogram of ibandronate sodium Form Q1.
Figure 12A:
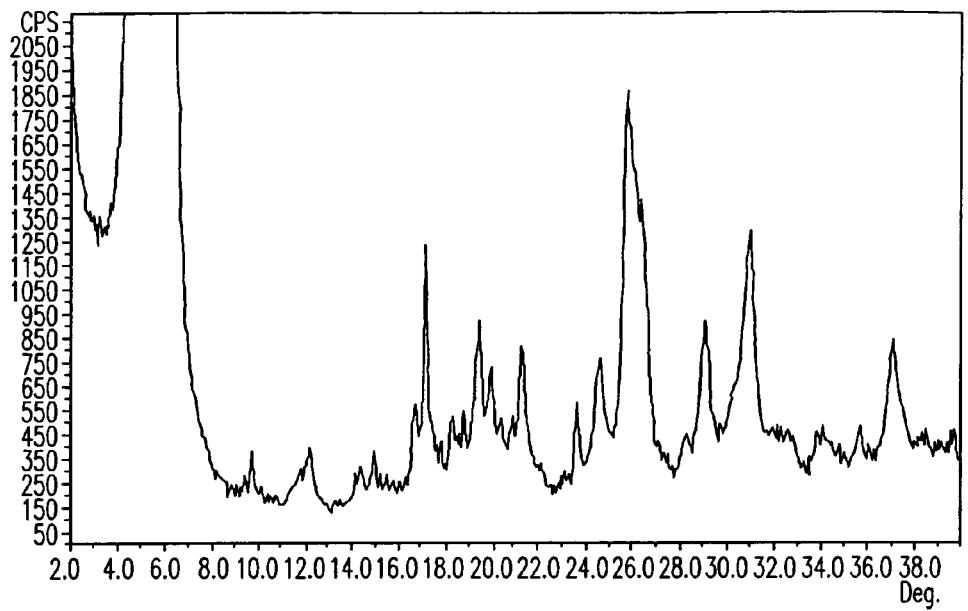
FIG. 12a is an x-ray powder diffractogram of ibandronate sodium Form Q1.

In another embodiment, the present invention provides a solid crystalline form of ibandronate sodium denominated Form Q1. Form Q1 is characterized by x-ray powder diffraction reflections at 4.7, 6.0, 17.2, 26.2, and 31.0±0.2 degrees two-theta. Form Q1 can be further characterized by x-ray powder diffraction reflections at 19.5, 21.4, 25.8, 29.1, and 37.1±0.2 degrees two-theta. FIGS. 12 and 12a show representative powder x-ray diffraction diagrams for Form Q1. Form Q1 can be in the range of a dihydrate to a trihydrate. Form Q1 can be further characterized by TGA, showing a weight loss of about 9 to about 16%.

Figure 13:
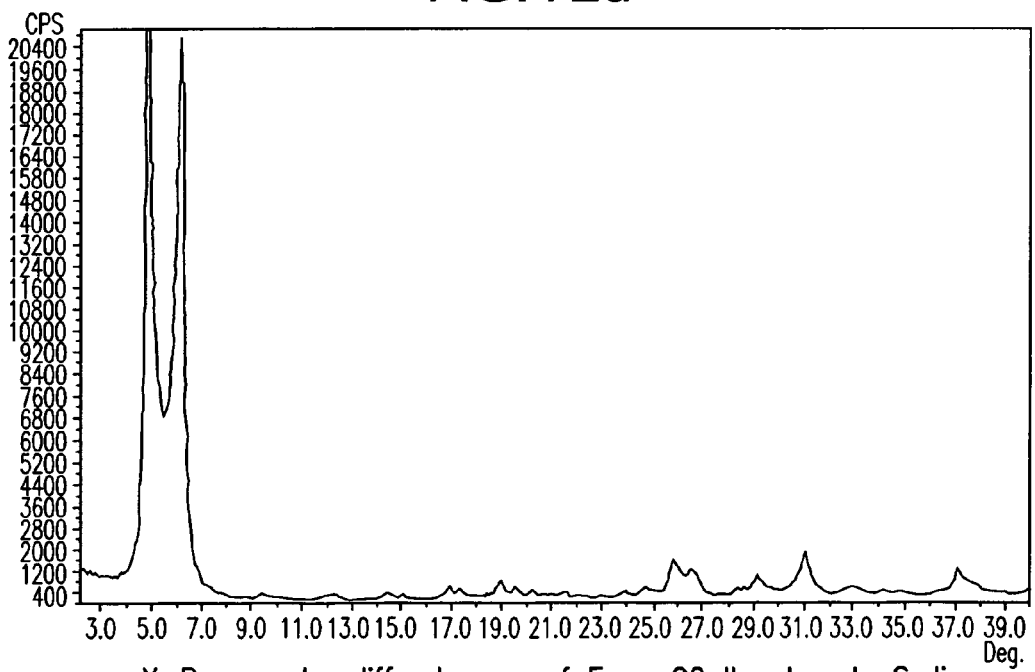
FIG. 13 is an x-ray powder diffractogram of ibandronate sodium Form Q2.
Figure 13A:
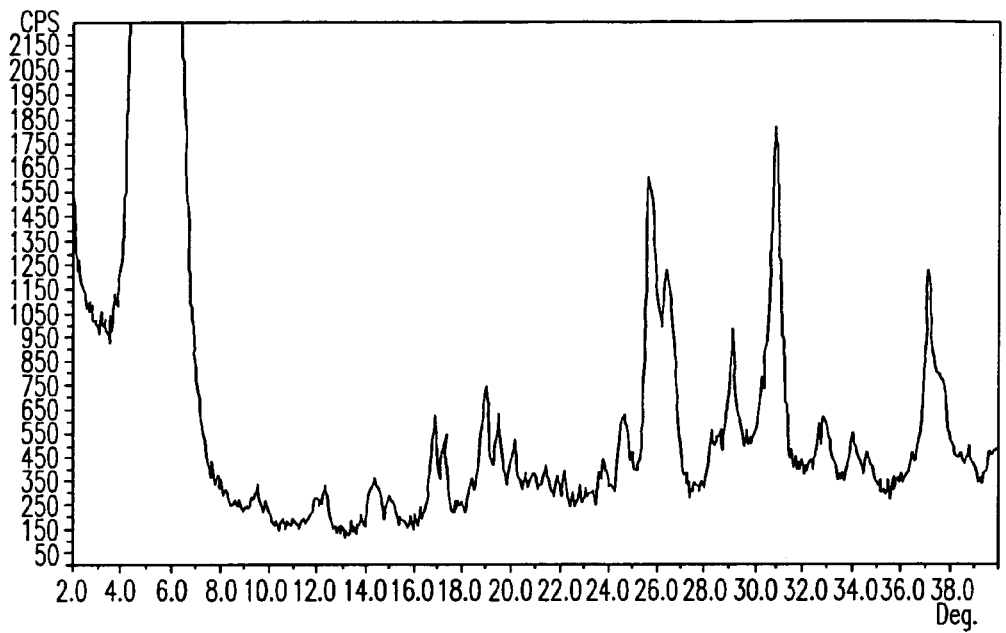
FIG. 13a is an x-ray powder diffractogram of ibandronate sodium Form Q2.

In another embodiment, the present invention provides a solid crystalline form of ibandronate sodium denominated Form Q2. Form Q2 is characterized by x-ray powder diffraction reflections at 4.9, 6.2, 25.9, 31.0, and 37.1±0.2 degrees two-theta. Form Q2 can be further characterized by x-ray powder diffraction reflections at 16.9, 17.3, 19.0, 26.6, and 29.2±0.2 degrees two-theta. FIGS. 13 and 13a show representative powder x-ray diffraction diagrams for Form Q2. Form Q2 can be a in the range of a dihydrate to a tetrahydrate. Form Q2 can be further characterized by TGA, showing a weight loss of about 8 to about 17%.

Figure 14:
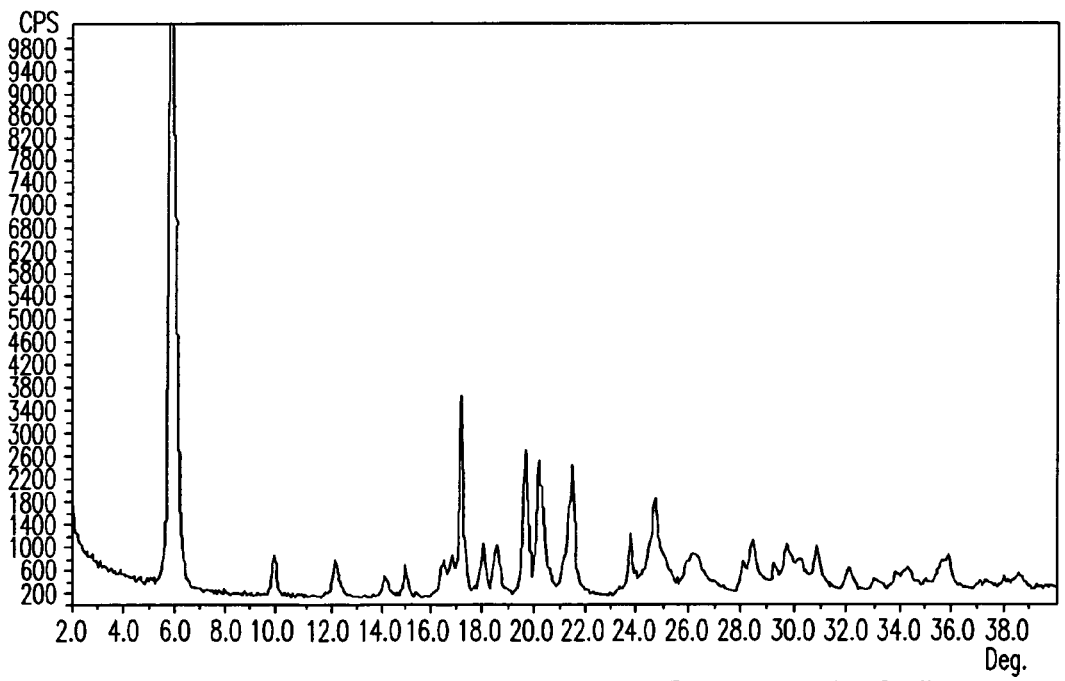
FIG. 14 is an x-ray powder diffractogram of ibandronate sodium Form Q3.

In another embodiment, the present invention provides a solid crystalline form of ibandronate sodium denominated Form Q3. Form Q3 is characterized by x-ray powder diffraction reflections at 5.9, 17.1, 19.6, 20.2, and 21.3±0.2 degrees two-theta. Form Q3 can be further characterized by x-ray powder diffraction reflections at 18.0, 18.5, 23.6, 24.7, and 30.8±0.2 degrees two-theta. FIG. 14 shows a representative powder x-ray diffraction diagram for Form Q3. Form Q3 can be further characterized by TGA, showing a weight loss of about 7 to about 9%.

Figure 15:
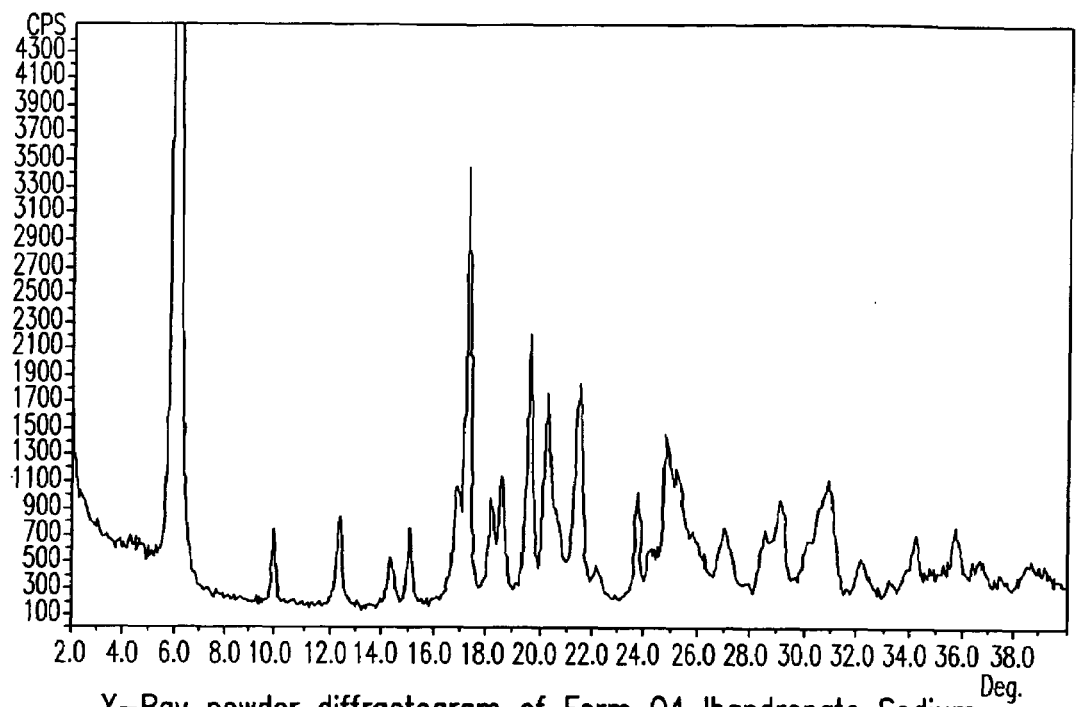
FIG. 15 is an x-ray powder diffractogram of ibandronate sodium Form Q4.

In another embodiment, the present invention provides a solid crystalline form of ibandronate sodium denominated Form Q4. Form Q4 is characterized by x-ray powder diffraction reflections at 6.1, 17.2, 19.6, 20.3, and 21.4±0.2 degrees two-theta. Form Q4 can be further characterized by x-ray powder diffraction reflections at 16.9, 18.1, 18.5, 23.7, and 24.8±0.2 degrees two-theta. FIG. 15 shows a representative powder x-ray diffraction diagram for Form Q4. Form Q4 can be further characterized by TGA, showing a weight loss of about 7 to about 8%.

Figure 16:
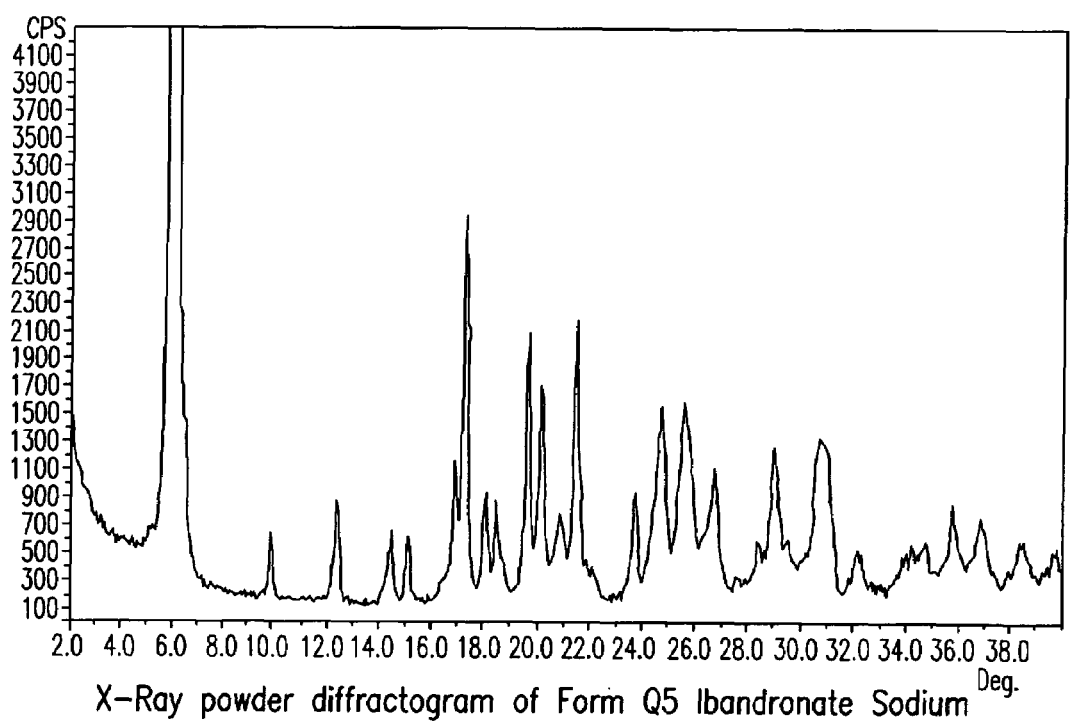
FIG. 16 is an x-ray powder diffractogram of ibandronate sodium Form Q5.

In another embodiment, the present invention provides a solid crystalline form of ibandronate sodium denominated Form Q5. Form Q5 is characterized by x-ray powder diffraction reflections at 6.1, 17.2, 19.6, 20.1, and 21.5±0.2 degrees two-theta. Form Q5 can be further characterized by x-ray powder diffraction reflections at 16.8, 24.7, 25.7, 29.0, and 30.9±0.2 degrees two-theta. FIG. 16 shows a representative powder x-ray diffraction diagram for Form Q5. Form Q5 can be further characterized by TGA, showing a weight loss of about 5 to about 11%.

Figure 17:
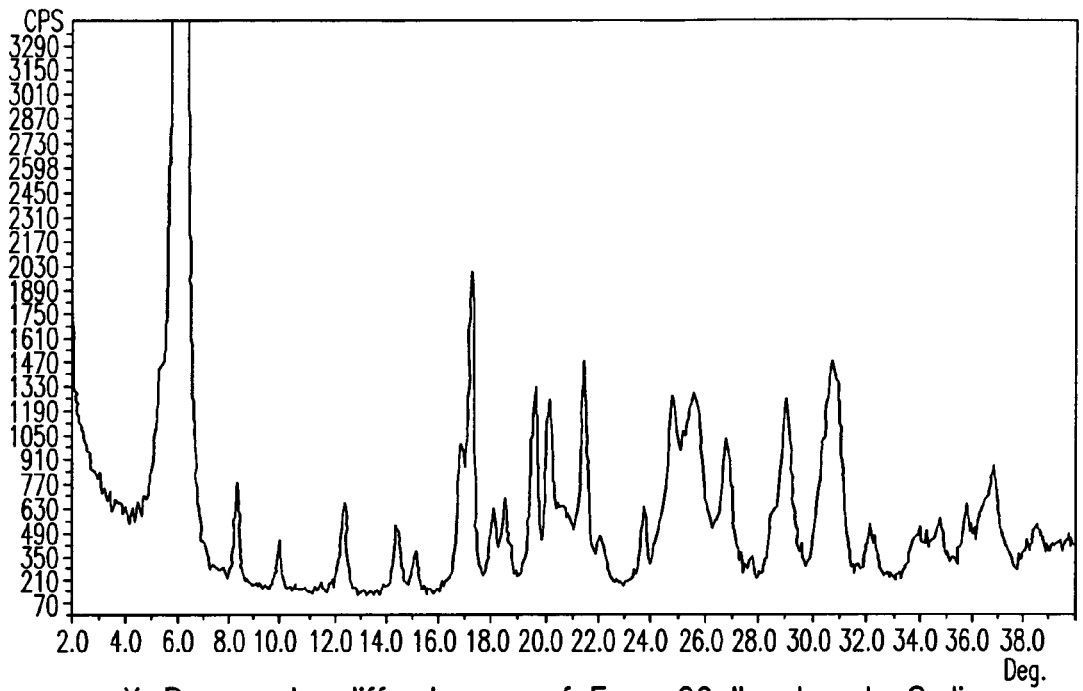
FIG. 17 is an x-ray powder diffractogram of ibandronate sodium Form Q6.

In another embodiment, the present invention provides a solid crystalline form of ibandronate sodium denominated Form Q6. Form Q6 is characterized by x-ray powder diffraction reflections at 6.1, 17.3, 19.6, 21.5, and 30.8±0.2 degrees two-theta. Form Q6 can be further characterized by x-ray powder diffraction reflections at 16.9, 20.2, 25.6, 26.9, and 29.1±0.2 degrees two-theta. FIG. 17 shows a representative powder x-ray diffraction diagram for Form Q6. Form Q6 can be further characterized by TGA, showing a weight loss of about 9 to about 10%.

Figure 18:
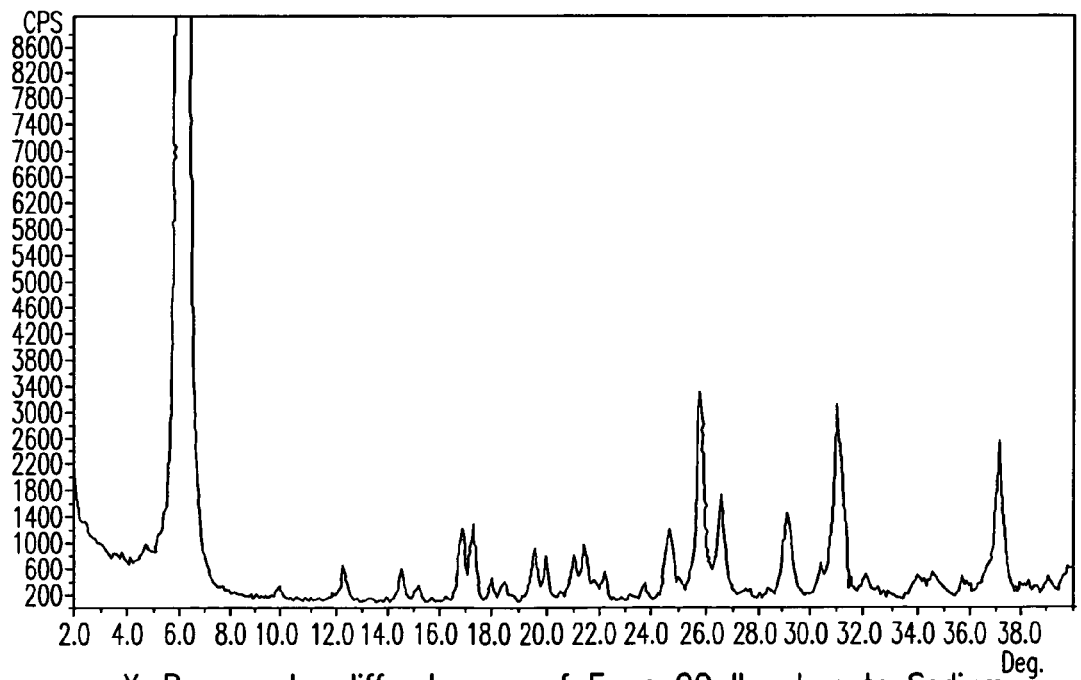
FIG. 18 is an x-ray powder diffractogram of ibandronate sodium Form QQ.

In another embodiment, the present invention provides a solid crystalline form of ibandronate sodium denominated Form QQ. Form QQ is characterized by x-ray powder diffraction reflections at 6.2, 25.9, 26.7, 31.1, and 37.2±0.2 degrees two-theta. Form QQ can be further characterized by x-ray powder diffraction reflections at 16.9, 17.3, 21.5, 24.7, and 29.2±0.2 degrees two-theta. FIG. 18 shows a representative powder x-ray diffraction diagram for Form QQ. This crystalline form does not transform into other polymorphic forms by more than 5% when stored, for example, under 100% relative humidity at 40° C. for 3 days. Form QQ also has a particle size distribution of not more than 100µ preferably not more than 60µ. Form Q2 can be a in the range of a monohydrate to a trihydrate. Form QQ can be further characterized by TGA, showing a weight loss of about 5 to about 12%.

An optical microscope can be used for directly observing and evaluating the maximum size and shape of particles. A suspension of material (as a sample in silicone fluid) can be placed on a slide and observed by different lenses of the microscope. The size of the particles can be estimated by a calibrated inner rule.

Figure 19:
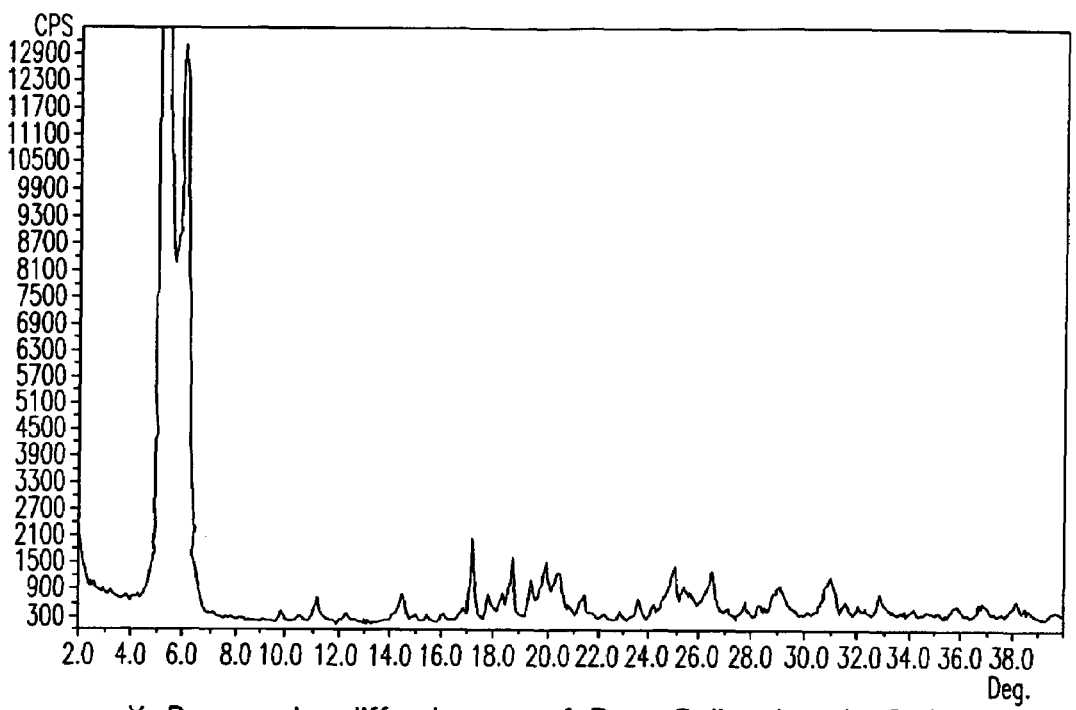
FIG. 19 is an x-ray powder diffractogram of ibandronate sodium Form R.

In another embodiment, the present invention provides a solid crystalline form of ibandronate sodium denominated Form R. Form R is characterized by x-ray powder diffraction reflections at 5.3, 6.0, 17.2, 18.7, and 20.0±0.2 degrees two-theta. Form R can be further characterized by x-ray powder diffraction reflections at 20.5, 25.0, 26.5, 29.1, and 31.0±0.2 degrees two-theta. FIG. 19 shows a representative powder x-ray diffraction diagram for Form R. Form R can be a hemiethanolate and/or monohydrate. Form R can be further characterized by TGA, showing a weight loss of about 10 to about 11%.

Figure 20:
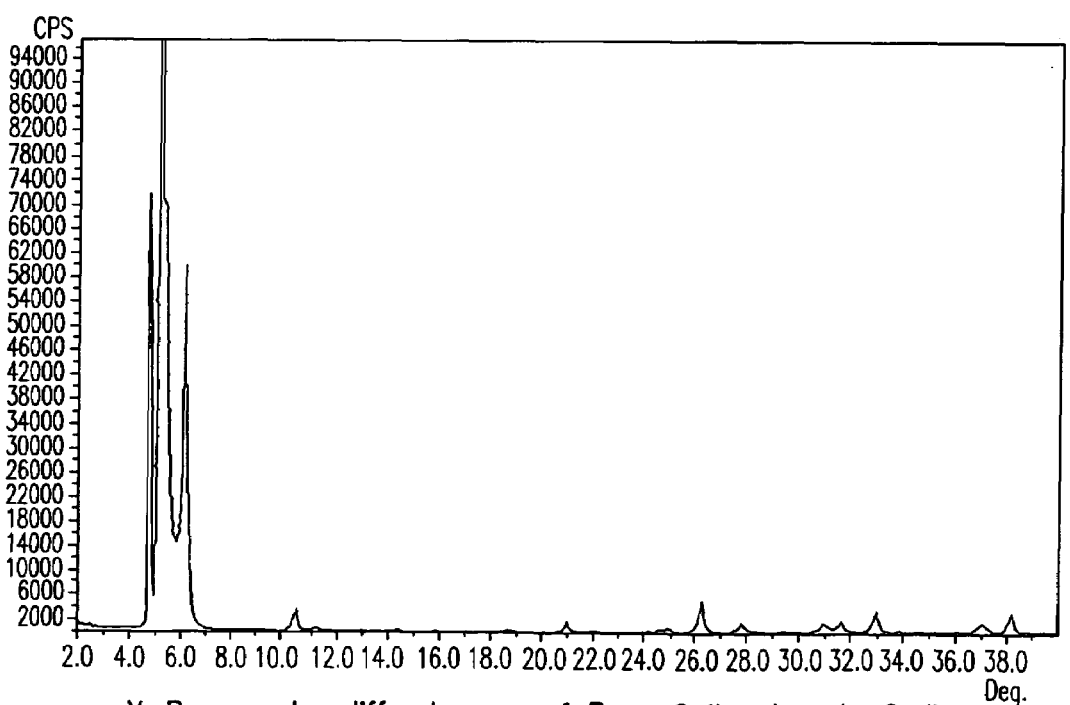
FIG. 20 is an x-ray powder diffractogram of ibandronate sodium Form S.
Figure 20A:
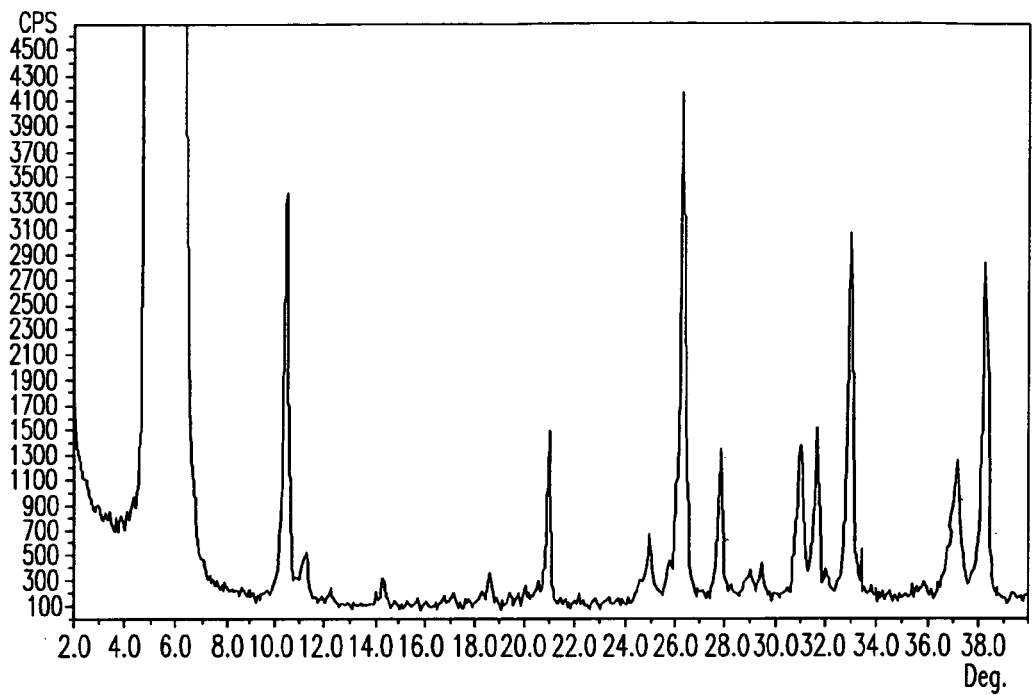
FIG. 20a is an x-ray powder diffractogram of ibandronate sodium Form S.

In another embodiment, the present invention provides a solid crystalline form of ibandronate sodium denominated Form S. Form S is characterized by x-ray powder diffraction reflections at 4.8, 5.1, 5.3, 5.4, and 6.1±0.2 degrees two-theta. Form S can be further characterized by x-ray powder diffraction reflections at 10.5, 21.0, 26.3, 33.0, and 38.2±0.2 degrees two-theta. FIGS. 20 and 20a show representative powder x-ray diffraction diagrams for Form S. Form S may be a hemiethanolate and/or hemihydrate. Form S can be further characterized by TGA, showing a weight loss of about 11 to about 12%.

Figure 21:
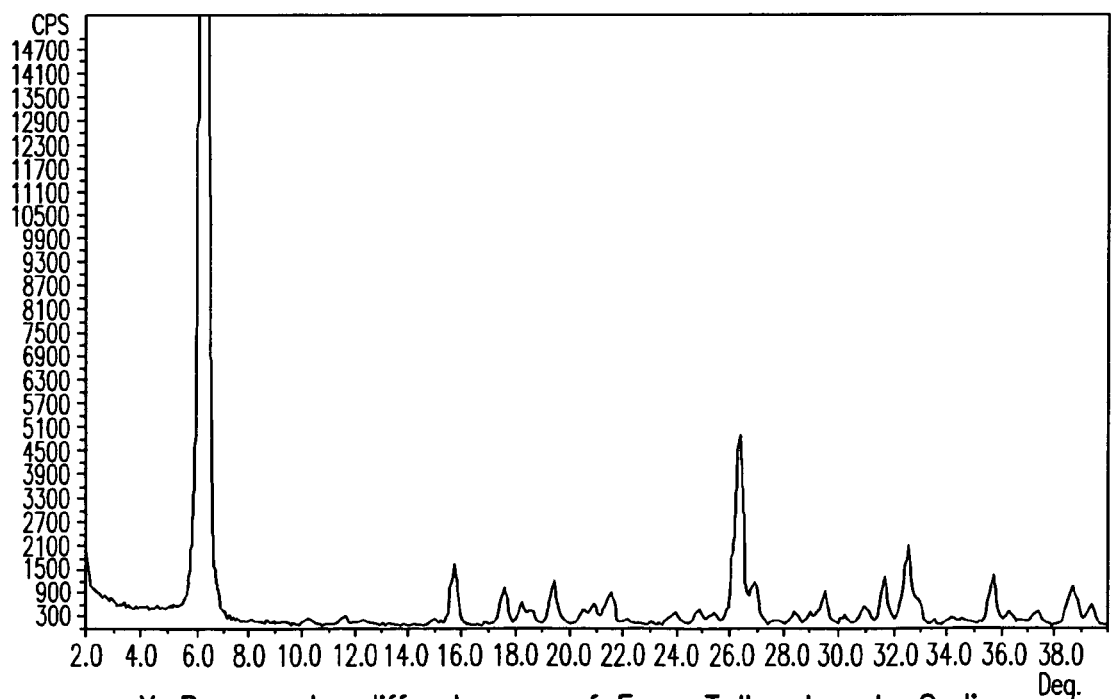
FIG. 21 is an x-ray powder diffractogram of ibandronate sodium Form T.

In another embodiment, the present invention provides a solid crystalline form of ibandronate sodium denominated Form T. Form T is characterized by x-ray powder diffraction reflections at 6.2, 15.7, 26.3, 32.6, and 35.6±0.2 degrees two-theta. Form T can be further characterized by x-ray powder diffraction reflections at 17.6, 19.4, 26.9, 31.7, and 38.7±0.2 degrees two-theta. FIG. 21 shows a representative powder x-ray diffraction diagram for Form T. Form T is can be further characterized by TGA, showing a weight loss of about 5 to about 7%.

Figure 22:
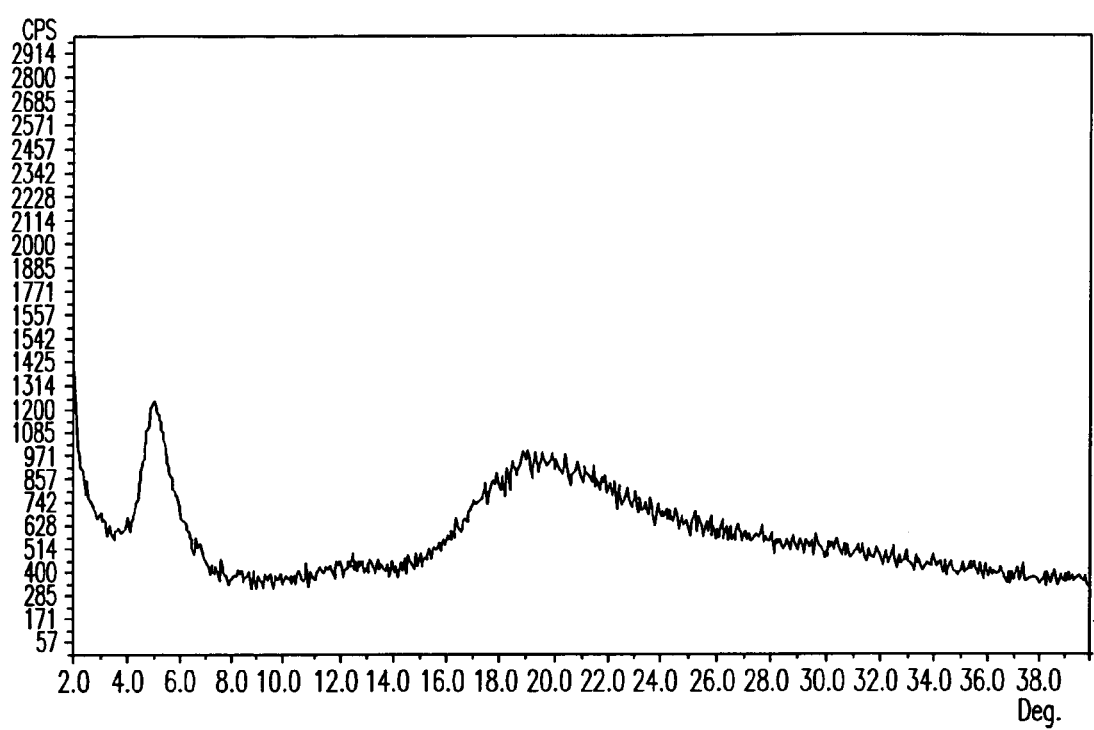
FIG. 22 is an x-ray powder diffractogram of amorphous ibandronate sodium.

In another embodiment, the present invention provides solid amorphous ibandronate sodium. FIG. 22 shows a representative powder x-ray diffraction diagram for amorphous ibandronate sodium. The amorphous form can be further characterized by TGA, showing a weight loss of about 6.8 to about 24.4%.

In another embodiment, the present invention provides processes for preparing crystalline forms of ibandronate sodium including the steps of dissolving ibandronate sodium in a solvent and isolating the crystalline form of ibandronate sodium from the reaction mixture.

In another embodiment, the present invention provides processes for preparing crystalline forms of ibandronate sodium including the steps of combining sodium hydroxide with ibandronic acid, preferably amorphous ibandronic acid, with a solvent and isolating the crystalline form of ibandronate sodium from the combination. The solvent can be an organic solvent such as a $C_3$-$C_7$ ketone or ester, a $C_1$-$C_3$ alcohol, or acetonitrile; water; or a mixture thereof. Preferred solvents for use in this embodiment of the present invention include acetone, methanol, ethanol, isopropanol, acetonitrile, water, and mixtures thereof. The sodium hydroxide can be solid, aqueous, or preferably, the sodium hydroxide is in solution in the solvent with which the sodium hydroxide and ibandronic acid are combined. The crystalline ibandronate sodium is preferably precipitated from a solution having a pH of about 3 to about 5, preferably about 4.

The initial combination can be and usually is a solution. The processes can further comprise combining the solution with an antisolvent. As used herein, an antisolvent is a liquid that causes a substance X to precipitate from a solution more rapidly or to a greater extent than X would precipitate from the same solution under the same conditions but without the antisolvent. A solution can be added to an antisolvent or vice versa. The antisolvent can be added dropwise or all at once. The antisolvent can be, for example, an organic solvent including a $C_3$-$C_7$ ketone or ester such as acetone; a $C_1$-$C_4$ alcohol such as methanol, ethanol, isopropanol, 1-butanol, or 2-butanol; DMSO; acetonitrile; tetrahydrofuran; or a $C_5$-$C_7$ cyclic or acyclic saturated hydrocarbon such as hexane.

The processes can also comprise heating the combination (which can be a solution) and/or cooling the combination. For example, the combination can be heated to a temperature above room temperature up to a temperature of about 50° C. to about 130° C., preferably about reflux temperature. The combination can be cooled to a temperature of about room temperature to about 0° C., preferably about room temperature. The solution can be cooled at once or stepwise. When a cooling step is used with the processes beginning with ibandronic acid and NaOH, the solution is preferably cooled stepwise, most preferably by first cooling to room temperature and then cooling further with an ice bath.

Preferably, the combination is a solution and the solution is stirred during one or more steps to facilitate complete precipitation. Preferably, the solution is stirred during one or more steps for about 10 minutes to about 72 hours, preferably about hour to about 20 hours, most preferably about 16 hours.

Isolating the crystalline form can be performed by any means known in the art. For example, the crystalline form can be isolated by suction filtration. The processes can also include washing and/or drying the precipitated crystalline form. For example, the crystalline form can be washed with the same solvent used for dissolution. It can be dried in a vacuum oven at about 50° C. for about 24 hours or it can be dried by evaporation.

In one embodiment, the present invention provides a process for preparing ibandronate sodium Form C including the steps of dissolving ibandronate sodium in dimethylsulfoxide (DMSO) to form a solution, combining the solution with butanol to form a slurry, and isolating ibandronate sodium Form C from the slurry. Preferably, the solution is heated to a temperature of about 120° C. to about 125° C. Preferably, the slurry is stirred at the heated temperature for about 1 to about 5 hours, more preferably about 3 hours. Preferably, the process further includes cooling the slurry to about room temperature.

In one embodiment, the present invention provides a process for preparing ibandronate sodium Form D including the steps of dissolving ibandronate sodium in water to form a solution, combining the solution with acetone to form a slurry, and isolating crystalline ibandronate sodium from the slurry. Preferably, the process includes heating the solution to about reflux temperature. Preferably, the slurry is stirred at about reflux temperature for about 1 to about 5 hours, preferably about 4.5 hours. Preferably, the process further includes cooling the slurry to about room temperature.

In another embodiment, the present invention provides a process for preparing ibandronate sodium Form E including the steps of dissolving ibandronate sodium in water to form a solution, combining the solution with methanol or 1-butanol to form a slurry, and isolating ibandronate sodium Form E from the slurry. The process can also include heating and cooling the solution. When the process includes heating the solution, the solution is preferably heated to about reflux temperature. When the solution is heated, the slurry is preferably stirred at about reflux temperature for about 1 to about 5 hours, more preferably about 4 to about 4.5 hours. The heated slurry can be further cooled to about room temperature. Optionally, when 1-butanol is used the process is done at about room temperature.

In one embodiment, the present invention provides a process for preparing ibandronate sodium Form F including the steps of dissolving ibandronate sodium in water to form a solution, combining the solution with isopropanol to form a slurry, and isolating ibandronate sodium Form F from the slurry. Preferably, the process includes heating the solution to about reflux temperature. Preferably, the slurry is stirred at about reflux temperature for about 1 to about 5 hours, more preferably about 4 hours. Preferably, the process further includes cooling the slurry to about room temperature.

In another embodiment, the present invention provides a process for preparing ibandronate sodium Form F including the steps of combining sodium hydroxide with ibandronic acid in a mixture of water and isopropanol having a ratio of water to isopropanol of about 20:80 to about 60:40, and isolating ibandronate sodium Form F from the reaction mixture. Preferably, the process includes heating the reaction mixture to about reflux temperature. Preferably, the reaction mixture is stirred at about reflux temperature for about 0.5 to about 5 hours. Preferably, the process further includes cooling the slurry to about room temperature.

In one embodiment, the present invention provides a process for preparing ibandronate sodium Form G including the steps of dissolving ibandronate sodium in water to form a solution, combining the solution with DMSO to form a slurry, and isolating ibandronate sodium Form G from the slurry. Preferably, the solution is at about room temperature. Preferably, the slurry is stirred at about room temperature for about 16 hours.

Alternatively, the process can include the steps of dissolving ibandronate sodium in DMSO to form a solution, combining the solution with ethanol to form a slurry, and isolating ibandronate sodium Form G from the solution. Preferably, the process includes heating the solution to about 120° C. to about 125° C., more preferably about 120° C. Preferably, the solution is further cooled to room temperature and stirred for about 16 hours. Preferably, the slurry is stirred at about room temperature for about 1 to about 3 hours, more preferably about 2 hours.

In one embodiment, the present invention provides a process for preparing ibandronate sodium Form H including the steps of dissolving ibandronate sodium in water to form a solution, combining the solution with methanol, ethanol, or isopropanol, to form a slurry, and isolating ibandronate sodium Form H from the slurry.

Preferably, the solution is at about room temperature. Preferably, the slurry is stirred for about 16 hours at about room temperature.

In one embodiment, the present invention provides a process for preparing ibandronate sodium Form J including the steps of dissolving ibandronate sodium in water to form a solution, combining the solution with DMSO to form a slurry, and isolating ibandronate sodium Form J from the slurry. Preferably, the process includes heating the solution to about reflux temperature. Preferably, the slurry is stirred at about reflux temperature for about 1 to about 10 hours, more preferably about 6 hours. Preferably, the process further includes cooling the slurry to about room temperature.

In another embodiment, the present invention provides a process for preparing ibandronate sodium Form K including the steps of combining sodium hydroxide with ibandronic acid in isopropanol and isolating ibandronate sodium Form K from the solution. Preferably, the process includes heating the reaction mixture to about reflux temperature. Preferably, the reaction mixture is stirred at about reflux temperature for about 1 to about 5 hours, more preferably about 4 hours. Preferably, the process further includes cooling the slurry to about room temperature.

In one embodiment, the present invention provides a process for preparing ibandronate sodium Form K2 including the steps of dissolving ibandronate sodium in water, and isolating ibandronate sodium Form K2 from the reaction mixture. Preferably, the process includes heating the reaction mixture to about reflux temperature. Preferably, the process further includes cooling the reaction mixture to about room temperature.

In another embodiment, the present invention provides a process for preparing ibandronate sodium Form K3 including the steps of combining sodium hydroxide with ibandronic acid in water to form a solution, combining the solution with isopropanol to form a slurry, and isolating ibandronate sodium Form K3 from the slurry. Preferably, the process includes heating the solution of ibandronic acid in water to about 70° C. Preferably, the isopropanol is cold, and the slurry is further cooled, preferably to about 0° C. Preferably, the slurry is stirred at about 0° C. for about 16 hours.

In one embodiment, the present invention provides a process for preparing ibandronate sodium Form Q including the steps of dissolving ibandronate sodium in water to form a solution, combining the solution with acetone or acetonitrile to form a slurry, and isolating ibandronate sodium Form Q from the solution. Preferably, the solution is at about room temperature. Preferably, the slurry is stirred at about room temperature for about 16 hours. Optionally, when the solvent is acetone, the solution is heated to about reflux temperature, and the slurry is stirred at about reflux temperature for about 4 to about 5 hours. Preferably, when the slurry is at about reflux temperature, the process further includes cooling the slurry to about room temperature.

In another embodiment, the present invention provides a process for preparing ibandronate sodium Form Q including the steps of combining sodium hydroxide with ibandronic acid in acetone, ethanol, water, or a mixture of water and acetonitrile having a ratio of water to acetonitrile of about 20:80 or about 60:40, and isolating ibandronate sodium Form Q from the reaction mixture. When the solvent is water, the process further includes the step of combining the reaction mixture with acetone. When the solvent is water, the reaction mixture is preferably at room temperature. When the solvent is acetone, ethanol, or a mixture of water and acetonitrile having a ratio of water to acetonitrile of about 20:80 or about 60:40, the reaction mixture is preferably at reflux temperature and afterwards, the reaction mixture is cooled to about room temperature.

In one embodiment, the present invention provides a process for preparing ibandronate sodium Form Q1 including the steps of dissolving ibandronate sodium in water to form a solution, combining the solution with 2-butanol or tetrahydrofuran to form a slurry, and isolating ibandronate sodium Form Q1 from the slurry. Preferably, the solution is at about room temperature. Preferably, the slurry is stirred at about room temperature for about 16 hours.

In one embodiment, the present invention provides a process for preparing ibandronate sodium Form Q2 including the steps of dissolving ibandronate sodium in water to form a solution, combining the solution with acetonitrile to form a slurry, and isolating ibandronate sodium Form Q2 from the slurry. Preferably, the process includes heating the reaction mixture to about reflux temperature. Preferably, the process includes stirring the slurry at about reflux temperature for about 1 to about 5 hours, preferably 4.5 hours. Preferably, the process further includes cooling the slurry to about room temperature.

In another embodiment, the present invention provides a process for preparing ibandronate sodium Form Q2 including the steps of combining sodium hydroxide with ibandronic acid in water to form a solution, combining the solution with 2-butanol, and isolating ibandronate sodium Form Q2 from the reaction mixture. Preferably, the solution is at about room temperature. Preferably, the reaction mixture is stirred at about room temperature for about 16 hours.

In another embodiment, the present invention provides a process for preparing ibandronate sodium Form Q3 including the steps of combining sodium hydroxide with ibandronic acid in methanol or a mixture of water and methanol having a ratio of water to methanol of about 60:40 and isolating ibandronate sodium Form Q3 from the reaction mixture. Preferably, the reaction mixture is heated to about reflux temperature. Preferably, the process includes stirring the reaction mixture at about reflux temperature for about 1 to about 5 hours. Preferably, the process further includes cooling the reaction mixture to about room temperature.

In another embodiment, the present invention provides a process for preparing ibandronate sodium Form Q4 including the steps of combining sodium hydroxide with ibandronic acid in water to form a solution, combining the solution with acetone, and isolating ibandronate sodium Form Q4 from the reaction mixture. Preferably, the solution is heated to about reflux temperature. Preferably, the acetone is a cold acetone. Preferably, when the acetone is added, the reaction mixture is stirred at about 0° C. to about 5° C., more preferably at about 3° C., for about 1 to about 5 hours, more preferably for about 2 hours.

In another embodiment, the present invention provides a process for preparing ibandronate sodium Form Q5 including the steps of combining sodium hydroxide with ibandronic acid in a mixture of water and acetonitrile having a ratio of water to acetonitrile of about 40:60, ethanol, or methanol and isolating ibandronate sodium Form Q5 from the reaction mixture. When the solvent is ethanol, the sodium hydroxide is preferably aqueous NaOH. Preferably, when the solvent is ethanol or methanol the reaction mixture is at about room temperature. Preferably, when the solvent water and acetonitrile having a ratio of water to acetonitrile of about 40:60, the reaction mixture is preferably heated to about reflux temperature and afterwards, the is cooled to about room temperature.

In another embodiment, the present invention provides a process for preparing ibandronate sodium Form Q6 including the steps of combining sodium hydroxide with ibandronic acid in about 96% ethanol and isolating ibandronate sodium Form Q6 from the reaction mixture. Preferably, the sodium hydroxide is added to a solution of ibandronic acid and 96% ethanol at about reflux temperature. Preferably, the process includes stirring the reaction mixture at about room temperature for about 10 to about 30 hours, preferably about 20 hours.

In one embodiment, the present invention provides a process for preparing ibandronate sodium Form QQ including the steps of dissolving ibandronate sodium in water to form a solution, combining the solution with THF to form a slurry, and isolating ibandronate sodium Form QQ from the slurry. Preferably, the slurry is stirred at about room temperature for about 16 hours.

In another embodiment, the present invention provides a process for preparing ibandronate sodium Form QQ including the steps of combining sodium hydroxide with ibandronic acid in a mixture of water and acetone having a ratio of water to acetone of about 40:60, ethanol, or water to form a solution and isolating ibandronate sodium Form QQ from the solution. When the solvent is ethanol, it is preferably about 93% ethanol. Alternatively, the solvent can be ethanol and the ibandronic acid is added in a solution with water. When the solvent is water, the ibandronic acid is added in a slurry with ethanol.

In yet another embodiment, the present invention provides a process for preparing ibandronate sodium Form QQ including the steps of dissolving ibandronate sodium in water to form a solution, maintaining the solution under a saturated environment of acetone, and decanting the solution to obtain ibandronate sodium Form QQ.

In one embodiment, the present invention provides a process for preparing ibandronate sodium Form R including the steps of dissolving ibandronate sodium in water to form a solution, combining the solution with ethanol to form a slurry, and isolating ibandronate sodium Form R from the slurry. Preferably, the slurry is stirred at room temperature for about 16 hours.

In another embodiment, the present invention provides a process for preparing ibandronate sodium Form R including the steps of combining sodium hydroxide with ibandronic acid in a mixture of water and ethanol having a ratio of water to ethanol of about 60:40 or a mixture of water and methanol having a ratio of water to methanol of about 20:80 to about 40:60 to and isolating ibandronate sodium Form R from the reaction mixture. Preferably, the reaction mixture is at about reflux temperature. Preferably, the process further includes cooling the reaction mixture to about room temperature.

In another embodiment, the present invention provides a process for preparing ibandronate sodium Form S including the steps of combining sodium hydroxide with ibandronic acid in a mixture of water and ethanol having a ratio of water to ethanol of about 40:60 and isolating ibandronate sodium Form S from the reaction mixture. Preferably, the process includes stirring the reaction mixture at about reflux temperature for about 1 to about 5 hours, most preferably about 3.5 hours.

In another embodiment, the present invention provides a process for preparing ibandronate sodium Form T including the steps of combining sodium hydroxide with ibandronic acid in a mixture of water and acetone having a ratio of water to acetone of about 20:80 and isolating ibandronate sodium Form T from the reaction mixture. Preferably, the process includes stirring the reaction mixture at about reflux temperature for about 1 to about 5 hours, most preferably about 1.5 hours. Preferably, the process further includes cooling the reaction mixture to about room temperature.

In one embodiment, the present invention provides a process for preparing amorphous ibandronate sodium including the steps of dissolving ibandronate sodium in DMSO to form a solution, combining the solution with acetone to form a slurry, and isolating amorphous ibandronate sodium from the slurry. Preferably, the process includes heating the solution to a temperature of about 120° C. Preferably, the slurry is stirred at about reflux temperature for about 10 minutes to about 5 hours, more preferably about 10 minutes to about 3.5 hours. Preferably, the process further includes cooling the solution to about room temperature.

In another embodiment, the present invention provides a process for preparing amorphous ibandronate sodium including the steps of combining sodium hydroxide with ibandronic acid in a mixture of water and ethanol having a ratio of water to ethanol of about 80:20, a mixture of water and isopropanol having a ratio of water to isopropanol of about 80:20, acetonitrile, a mixture of water and acetonitrile having a ratio of water to acetonitrile of about 60:40 to about 80:20, or water and isolating amorphous ibandronate sodium from the reaction mixture. The process can further include combining the solution with an antisolvent. For example, when the solvent is acetonitrile, acetone can be combined with the reaction mixture. When the solvent is water, hexanes can be combined with the solution.

In one embodiment, amorphous ibandronate sodium is obtained by spray drying a solution of ibandronate sodium. The term "spray drying" broadly refers to processes involving breaking up liquid mixtures into small droplets (atomization) and rapidly removing solvent from the mixture. In a typical spray drying apparatus, a strong driving force evaporates the solvent from the droplets, which can be provided by providing a drying gas. Spray drying can be performed in a conventional manner in the processes of the present invention, see, Remington: The Science and Practice of Pharmacy 681 (20th ed., 2000). The drying gas used in the invention can be any suitable gas, although inert gases such as nitrogen, nitrogen-enriched air, and argon are preferred. Nitrogen gas is a particularly preferred drying gas for use in the process of the invention. The ibandronate sodium product produced by spray drying can be recovered by techniques commonly used in the art, such as using a cyclone or a filter. Preferably, amorphous ibandronate sodium is obtained by spray drying a solution of ibandronate sodium in water.

Pharmaceutical formulations of the present invention contain crystalline ibandronate sodium, such as a form disclosed herein, or amorphous ibandronate sodium, and optionally one or more other forms of ibandronate sodium. In addition to the active ingredient, the pharmaceutical formulations of the present invention can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®, and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, ibandronate sodium and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

The present invention also provides methods comprising administering a pharmaceutical formulation of ibandronate sodium. Ibandronate sodium is preferably formulated for administration to a mammal, preferably a human, by injection. Ibandronate sodium can be formulated, for example, as a viscous liquid solution or suspension, preferably a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., *Pharmaceutical Dosage Forms and Drug Delivery Systems*, 7th ed.

Boniva® and/or Bondronat® can be used as guidance for formulation. Boniva® is available as an intravenous injection administered every 2-3 months and as an oral formulation. Bondronat® is available in ampoule with 1 ml concentrate for solution for infusion contains 1.125 mg of ibandronic monosodium salt monohydrate, corresponding to 1 mg of ibandronic acid.

Having described the invention, the invention is further illustrated by the following non-limiting examples. Table 1 presents a summary of the Examples, described in further detail below.

TABLE 1

| Form | Example | Residual solvent | Loss on dry by TGA [%] | DSC pT | DSC dH | Solvate/Hydrate |
|------|---------|------------------|-----------------------|--------|--------|-----------------|
| C | 1 | 11.1% | 15.0% | 183.1 | −105.8 | monoethanolate |
|   |   |       |        | 197.8 | −32.2  |                 |
| C | 2 |       | 16.0%  | 118.7 | −3.6   |                 |
|   |   |       |        | 183.7 | −129.3 |                 |
| D | 3 |       | 25.0%  | 102.1 | −4.7   |                 |
|   |   |       |        | 130.4 | −1.9   |                 |
|   |   |       |        | 164.5 | −123.2 |                 |
| E | 4 |       | 14.4%  | 79.6  | −3.0   |                 |
|   |   |       |        | 126.9 | −1.1   |                 |
|   |   |       |        | 144.9 | −9.1   |                 |
|   |   |       |        | 190.5 | −74.4  |                 |
|   |   |       |        | 205.8 | −41.5  |                 |
| E | 5 | 9.1%  | 15.8%  | 126.9 | −5.0   | hemibutanolate  |
|   |   |       |        | 192.0 | −114.0 |                 |
|   |   |       |        | 204.8 | −33.7  |                 |
| E | 6 |       | 20.7%  | 191.9 | −13.0  |                 |
| F | 7 |       | 14.8%  | 101.7 | −1.5   |                 |
|   |   |       |        | 142.3 | −7.9   |                 |
|   |   |       |        | 181.2 | −55.0  |                 |
|   |   |       |        | 193.9 | −34.3  |                 |
| F | 8 |       | 13.6%  | 142.9 | −1.1   |                 |
|   |   |       |        | 193.0 | −97.2  |                 |
|   |   |       |        | 198.6 | −57.9  |                 |
| F | 9 |       | 16.4%  | 143.2 | −1.2   |                 |
|   |   |       |        | 203.9 | −177.1 |                 |
| F | 10 |      | 31.4%  | 149.4 | −3.2   |                 |
|   |   |       |        | 177.9 | −24.8  |                 |
|   |   |       |        | 188.7 | −31.2  |                 |
|   |   |       |        | 196.5 | −54.4  |                 |
| G | 11 | 0.0% | 22.4%  | 151.5 | −173.7 |                 |
| G | 12 |      | 25.0%  | 75.9  | −9.9   |                 |
|   |   |       |        | 148.4 | −165.8 |                 |
| H | 13 |      | 15.6%  | 141.1 | −44.7  |                 |
|   |   |       |        | 183.9 | −120.9 |                 |
|   |   |       |        | 204.8 | −35.0  |                 |
| H | 14 |      | 14.5%  | 187.0 | −90.2  |                 |
|   |   |       |        | 202.2 | −19.9  |                 |
| H | 15 |      | 13.8%  | 191.7 | −81.4  |                 |
|   |   |       |        | 203.8 | −55.8  |                 |
| J | 16 | 0.1% | 22.8%  | 151.1 | −254.1 |                 |
|   |   |       |        | 188.6 | −17.5  |                 |
| K | 17 |      | 14.0%  | 70.2  | −8.0   |                 |
|   |   |       |        | 167.7 | −13.0  |                 |
|   |   |       |        | 183.2 | −73.5  |                 |
|   |   |       |        | 194.4 | −54.2  |                 |
| K2 | 18 |     | 9.3%   | 164.4 | −95.5  |                 |
|   |   |       |        | 192.1 | −41.9  |                 |
| K3 | 19 |     | 7.6%   | 154.8 | −43.7  |                 |
|   |   |       |        | 201.2 | −38.5  |                 |

TABLE 1-continued

| Form | Example | Residual solvent | Loss on dry by TGA [%] | DSC pT | dH | Solvate/Hydrate |
|---|---|---|---|---|---|---|
| Q | 20 | 0.6% | 9.3% | 153.5 | −99.8 | |
| | | | | 179.1 | −73.2 | |
| Q | 21 | | 15.9% | 149.6 | −4.9 | |
| | | | | 177.3 | −79.1 | |
| | | | | 190.3 | −36.5 | |
| Q | 22 | 0.0% | 24.1% | 102.1 | −4.7 | |
| | | | | 130.4 | −1.9 | |
| | | | | 164.5 | −123.2 | |
| Q | 23 | | 8.2% | 73.3 | −0.9 | |
| | | | | 154.1 | −135.6 | |
| | | | | 184.2 | −1.4 | |
| Q | 24 | | 10.1% | 80.3 | −2.7 | |
| | | | | 159.1 | −142.1 | |
| Q | 25 | | 6.7% | 163.8 | −66.6 | |
| | | | | 171.0 | −78.2 | |
| Q | 26 | | 5.9% | 156.0 | −97.1 | |
| | | | | 175.3 | −80.4 | |
| Q | 27 | | 5.8% | 178.0 | −143.5 | |
| Q1 | 28 | 0.9% | 15.9% | 145.1 | −5.2 | |
| | | | | 180.0 | −76.0 | |
| | | | | 190.5 | −33.0 | |
| Q1 | 29 | | 9.3% | 163.1 | −32.3 | |
| | | | | 189.7 | −122.7 | |
| | | | | 197.9 | −88.4 | |
| Q2 | 30 | 0.9% | 8.8% | 156.3 | −12.1 | |
| | | | | 176.7 | −53.3 | |
| | | | | 191.0 | −34.6 | |
| Q2 | 31 | | 16.9% | 131.1 | −20.4 | |
| | | | | 184.1 | −76.9 | |
| | | | | 192.5 | −56.2 | |
| Q3 | 32 | | 8.4% | 127.3 | +24.2 | |
| | | | | 178.4 | −87.3 | |
| | | | | 201.1 | +5.4 | |
| Q3 | 33 | | 7.7% | 177.6 | −61.3 | |
| | | | | 196.8 | −39.1 | |
| Q4 | 34 | | 7.7% | 162.6 | −103.1 | |
| Q5 | 35 | | 5.7% | 166.1 | −78.1 | |
| | | | | 173.4 | −71.3 | |
| Q5 | 36 | | 10.9% | 86.7 | −1.6 | |
| | | | | 166.8 | −136.8 | |
| | | | | 193.1 | −41.1 | |
| Q5 | 37 | | 7.3% | 159.8 | −127.6 | |
| Q6 | 38 | | 9.3% | 165.9 | −83.7 | |
| | | | | 192.2 | −4.6 | |
| QQ | 39 | | 5.6% | 143.8 | −128.0 | |
| | | | | 175.6 | −29.0 | |
| QQ | 40 | | 6.1% | 133.1 | −7.9 | |
| | | | | 173.9 | −149.3 | |
| QQ | | | 6.0% | 160.5 | −96.6 | |
| | | | | 176.4 | −97.0 | |
| QQ | 41 | | 8.8% | 131.6 | −14.1 | |
| | | | | 173.0 | −98.5 | |
| | | | | 193.1 | −39.4 | |
| QQ | 42 | | 6.3% | 163.6 | −70.9 | |
| | | | | 180.4 | −94.5 | |
| QQ | 43 | | 9.6% | 153.2 | −123.4 | |
| | | | | 167.2 | −46.5 | |
| | | | | 178.0 | −20.4 | |
| QQ | 44 | | 11.4% | 141.6 | −21.0 | |
| | | | | 167.0 | −23.5 | |
| | | | | 192.3 | −72.9 | |
| | | | | 200.2 | −65.4 | |
| R | 45 | 10.5% | 15.6% | 141.1 | −44.7 | Monoethanolate |
| | | | | 183.9 | −120.9 | |
| | | | | 204.8 | −35.0 | |
| R | 46 | 4.6% | 10.3% | 165.9 | −54.9 | 1/3 ethanolate |
| | | | | 196.5 | −52.9 | |
| R | 47 | | 10.4% | 171.6 | −75.4 | |
| | | | | 195.7 | −23.2 | |
| R | 48 | | 10.5% | 161.5 | −30.0 | |
| | | | | 174.5 | −39.1 | |
| | | | | 183.4 | −63.6 | |
| R | 49 | | 10.5% | 158.3 | −12.1 | |
| | | | | 177.2 | −83.2 | |
| | | | | 197.9 | −24.5 | |

TABLE 1-continued

| Form | Example | Residual solvent | Loss on dry by TGA [%] | DSC pT | DSC dH | Solvate/Hydrate |
|---|---|---|---|---|---|---|
| R | 50 | | 10.3% | 133.1 | −7.9 | |
| | | | | 173.9 | −149.3 | |
| S | 51 | 8.6% | 11.4% | 150.4 | −0.9 | Monoethanolate |
| | | | | 200.9 | −188.4 | |
| T | 52 | | 6.0% | 174.0 | −149.2 | |
| Amorphous | 53 | | 24.4% | 54.6 | +28.6 | |
| | | | | 88.5 | −143.6 | |
| | | | | 145.4 | −133.2 | |
| Amorphous | 54 | | 16.2% | 66.7 | +26.3 | |
| | | | | 92.5 | −94.6 | |
| | | | | 150.0 | −92.8 | |
| Amorphous | 55 | | | 56.6 | −21.1 | |
| | | | | 88.2 | −84.6 | |
| Amorphous | 56 | | 7.8% | 177.5 | −31.7 | |
| | | | | 60.5 | −32.0 | |
| | | | | 81.2 | −63.9 | |
| Amorphous | 57 | | 8.4% | 133.3 | −2.9 | |
| | | | | 80.7 | −95.2 | |
| Amorphous | 58 | | 10.0% | 152.7 | −2.0 | |
| | | | 8.4% | 56.0 | −11.3 | |
| | | | | 105.2 | −66.4 | |
| Amorphous | 59 | | 8.0% | 51.5 | −6.9 | |
| | | | | 105.4 | −9.0 | |
| | | | | 163.5 | −55.1 | |
| Amorphous | 60 | | 7.3% | 83.3 | −268.1 | |
| Amorphous | 61 | | 7.2% | 56.0 | −2.5 | |
| | | | | 96.2 | −88.8 | |
| Amorphous | 62 | | 9.1% | 100.8 | −321.0 | |
| | | | | 180.9 | +180.9 | |
| | | | | 214.8 | −5.0 | |
| Amorphous | 63 | | 6.8% | 47.4 | −3.1 | |
| | | | | 99.1 | −112.0 | |

EXAMPLES

X-Ray Powder Diffraction:

X-ray powder diffraction data were obtained by methods known in the art using a SCINTAG powder x-ray diffractometer model X'TRA equipped with a solid state detector. Copper radiation of 1.5418 Å was used. A round aluminum sample holder with round zero background quartz plate, with cavity of 25 (diameter)*0.5 (depth) mm.

Scanning Parameters:

Range: 2-40 degrees two-theta (±0.2 degrees two-theta)
Scan mode: Continuous scan.
Step size: 0.05 deg.
Scan rate: 5 deg./min.

Thermal Gravimetric Analysis (TGA):

Thermogravimetric analysis (TGA) was performed at a heating rate of 10° C./min. using a Mettler model TG50 instrument. The sample size was 7-15 mg.

In certain examples that employ a reflux medium, the reflux medium is a mixture of solvents. The composition of such mixed-solvent reflux media is expressed as a ratio on a volume per volume basis (v/v). The amount of water that should be added to the reflux media is calculated according to the following formula:

(10 volumes of alcohol per grams of $IBD-Ac \times 100)/X$ % of alcohol=$Y$ when Y is the total amount of alcohol and water together $Y \times (100-X)$ % of water/100=$Z$ when Z is the volume of water that should be added.

Differential Scanning Calorimetry

Differential scanning calorimetric (DSC) analysis was performed with a Mettler Toledo DSC 821$^e$ calorimeter. Samples of about 3 to about 5 milligrams, held in a vented (3-hole) crucible, were analyzed at a heating rate of 10° per minute.

Spray Drying

Spray drying was performed on a Buchi Mini Spray dryer B-290 with an evaporating capacity of 1 L/hr for water and higher for organic solvents. The maximum temperature input was 220° C., the air flow was at a maximum of 35 m$^2$/hr, and the spray gas was compressed air or nitrogen at 200-800 L/hr and 5-8 bar. The nozzle diameter was 0.7 mm (standard), and the nozzle cap was 1.4 mm and 1.5 mm.

Ibandronate Sodium Form C

Example 1

Ibandronate sodium (3 g) was dissolved in dimethylsulfoxide (DMSO) (20 ml) at 125° C. To the obtained solution, 2-butanol (40 ml) was added dropwise to obtain a white precipitate. The slurry was stirred at 125° C. for 3 hours, then cooled to room temperature and stirred for 16 hours. The precipitate was isolated by vacuum filtration, washed with 2-butanol (2×5 ml), and dried in a vacuum oven at 50° C. for 24 hours to obtain 3 g of ibandronate sodium crystal form C. Form C can exhibit a weight loss of about 15% to about 16% in TGA, performed as described above.

Example 2

Ibandronate sodium (3 g) was dissolved in DMSO (20 ml) at 120° C. To the obtained solution, 1-butanol (40 ml) was added dropwise to obtain a white precipitate. The slurry was stirred at 120° C. for 3 hours, then cooled to room temperature and stirred for 16 hours. The precipitate was isolated by vacuum filtration, washed with 1-butanol (2×5 ml), and dried in a vacuum oven at 50° C. for 24 hours to obtain 3 g of ibandronate sodium crystal form C.

Ibandronate Sodium Form D

Example 3

Ibandronate sodium (3 g) was dissolved in water (6 ml) at reflux temperature. To the obtained solution, acetone (50 ml) was added dropwise at reflux temperature to obtain a white precipitate. The slurry was stirred at reflux temperature for 4.5 hours, then cooled to room temperature. The precipitate was isolated by vacuum filtration, washed with acetone (3×13 ml), and dried in a vacuum oven at 50° C. for 22 hours to obtain 3.3 g of ibandronate sodium crystal form D. Form D can exhibit a weight loss of about 25% in TGA.

Ibandronate Sodium Form E

Example 4

Ibandronate sodium (3 g) was dissolved in water (6 ml) at reflux temperature. To the obtained solution, methanol (45 ml) was added dropwise at reflux temperature to obtain a white precipitate. The slurry was stirred at reflux temperature for 4.5 hours, then cooled to room temperature. The precipitate was isolated by vacuum filtration, washed with methanol (2×20 ml), and dried in a vacuum oven at 50° C. for 26 hours to obtain 2.95 g of ibandronate sodium crystal form E. Form E can exhibit a weight loss of about 14% to about 21% in TGA.

Example 5

Ibandronate sodium (3 g) was dissolved in water (18 ml) at room temperature. To the obtained solution, 1-butanol (40 ml) was added to obtain a white precipitate. The slurry was stirred at room temperature for 16 hours. The precipitate was isolated by vacuum filtration, washed with 1-butanol (2×16 ml), and dried in a vacuum oven at 50° C. for 23 hours to obtain 2.3 g of ibandronate sodium crystal form E.

Example 6

Ibandronate sodium (3 g) was dissolved in water (6 ml) at reflux temperature. To the obtained solution, 1-butanol (50 ml) was added dropwise to obtain a white precipitate. The slurry was stirred at reflux temperature for 4 hours, then cooled to room temperature. The precipitate was isolated by vacuum filtration, washed with 1-butanol (2×20 ml), and dried in a vacuum oven at 50° C. for 19 hours to obtain 2.8 g of ibandronate sodium crystal form E.

Ibandronate Sodium Form F

Example 7

Ibandronate sodium (3 g) was dissolved in water (6 ml) at reflux temperature. To the obtained solution, isopropanol (IPA) (50 ml) was added dropwise to obtain a white precipitate. The slurry was stirred at reflux temperature for 4 hours, then cooled to room temperature and stirred for 16 hours. The precipitate was isolated by vacuum filtration, washed with IPA (2×20 ml), and dried in a vacuum oven at 50° C. for 24 hours to obtain 3 g of ibandronate sodium crystal form F. Form F can exhibit a weight loss of about 13% to about 32% in TGA.

Example 8

A solution of sodium hydroxide (0.63 g) in water:IPA (20:80 v/v, 9.5 ml) was added dropwise to a solution of amorphous ibandronic acid (5 g) in water:IPA (20:80 v/v, 53 ml) at reflux temperature. The reaction mixture was heated at reflux temperature for an additional 4 hours to obtain a pH of 3.93-4.01. Then the reaction mixture was cooled to room temperature and stirred for 72 hours. Further cooling was performed using an ice-bath. The precipitate was filtered, washed with IPA (2×25 ml), and dried in a vacuum oven at 50° C. for 24 hours to give 4.4 g of ibandronate sodium crystal form F.

Example 9

A solution of sodium hydroxide (0.63 g) in water:IPA (40:60 v/v, 12 ml) was added dropwise to a solution of amorphous ibandronic acid (5 g) in water:IPA (40:60 v/v, 71 ml) at reflux temperature. The reaction mixture was heated at reflux temperature for an additional 4 hours to obtain a pH of 4.0-4.12. Then the reaction mixture was cooled to room temperature and stirred for 16 hours. Further cooling was performed using an ice-bath. The precipitate was filtered, washed with IPA (2×25 ml), and dried in a vacuum oven at 50° C. for 24 hours to give 4.3 g of ibandronate sodium crystal form F.

Example 10

A solution of sodium hydroxide (0.63 g) in water:IPA (60:40 v/v, 19 ml) was added dropwise to a solution of amorphous ibandronic acid (5 g) in water:IPA (60:40 v/v, 106 ml) at reflux temperature. The reaction mixture was heated at reflux temperature for an additional 30 minutes to obtain a pH of 4.14. Then the reaction mixture was cooled to room temperature and stirred for 16 hours. Further cooling was performed using an ice-bath. The precipitate was filtered, washed with IPA (2×25 ml), and dried in a vacuum oven at 50° C. for 23 hours to give 5.2 g of ibandronate sodium crystal form F.

Ibandronate Sodium Form G

Example 11

Ibandronate sodium (3 g) was dissolved in water (18 ml) at room temperature. To the obtained solution, DMSO (40 ml) was added in one portion to obtain a white precipitate. The slurry was stirred at room temperature for 16 hours. The precipitate was isolated by vacuum filtration, washed with DMSO (2×17 ml), and dried in a vacuum oven at 50° C. for 23 hours to obtain 2.5 g of ibandronate sodium crystal form G. Form G can exhibit a weight loss of about 22% to about 25% in TGA.

Example 12

Ibandronate sodium (3 g) was dissolved in DMSO (60 ml) at 120° C. The obtained solution was stirred at 120° C. for 25 minutes. The solution was cooled to room temperature and stirred for 16 hours. Ethanol (250 ml) was added in one portion to obtain a precipitate. The slurry was stirred at room temperature for 2 hours. Then the precipitate was isolated by vacuum filtration and dried in a vacuum oven at 50° C. for 24 hours to obtain 3.3 g of ibandronate sodium crystal form G.

Ibandronate Sodium Form H

Example 13

Ibandronate sodium (3 g) was dissolved in water (18 ml) at room temperature. To the obtained solution, ethanol (40 ml) was added in one portion to obtain a white precipitate. The slurry was stirred at room temperature for 16 hours. The precipitate was isolated by vacuum filtration, washed with ethanol (2×20 ml), and dried in a vacuum oven at 50° C. for 28 hours to obtain 2.5 g of ibandronate sodium crystal form H. Form H can exhibit a weight loss of about 13% to about 16%, or less in TGA.

Example 14

Ibandronate sodium (3 g) was dissolved in water (18 ml) at room temperature. To the obtained solution, IPA (40 ml) was added in one portion to obtain a white precipitate. The slurry was stirred at room temperature for 16 hours. The precipitate was isolated by vacuum filtration, washed with IPA (2×20 ml), and dried in a vacuum oven at 50° C. for 27 hours to obtain 2.2 g of ibandronate sodium crystal form H.

Example 15

Ibandronate sodium (3 g) was dissolved in water (18 ml) at room temperature. To the obtained solution, methanol (40 ml) was added in one portion to obtain a white precipitate. The slurry was stirred at room temperature for 16 hours. The precipitate was isolated by vacuum filtration, washed with methanol (2×30 ml), and dried in a vacuum oven at 50° C. for 27 hours to obtain 2.5 g of ibandronate sodium crystal form H.

Ibandronate Sodium Form J

Example 16

Ibandronate sodium (3 g) was dissolved in water (6 ml) at reflux temperature. To the obtained solution, DMSO (45 ml) was added dropwise to obtain a white precipitate. The slurry was stirred at reflux temperature for 6 hours, then cooled to room temperature and stirred for 16 hours. The precipitate was isolated by vacuum filtration, washed with DMSO (2×20 ml), and dried in a vacuum oven at 50° C. for 25 hours to obtain 3.1 g of ibandronate sodium crystal form J. Form J can exhibit a weight loss of about 22% to about 23% in TGA.

Ibandronate Sodium Form K

Example 17

A slurry of amorphous ibandronic acid (5 g) in IPA (50 ml) was heated to reflux temperature. Sodium hydroxide (0.63 g, solid) was added, and the reaction mixture was heated at reflux temperature for an additional 4 hours to obtain a pH of 4.19. Then the reaction mixture was cooled to room temperature. Further cooling was performed using an ice-bath. The precipitate was filtered, washed with IPA (2×25 ml), and dried in a vacuum oven at 50° C. for 24 hours to give 5.5 g of ibandronate sodium crystal form K. Form K can exhibit a weight loss of about 10% to about 14% in TGA.

Ibandronate Sodium Form K2

Example 18

Ibandronate sodium (3 g) was dissolved in water (6 ml) at reflux temperature. The solution was cooled to room temperature. The resulting precipitate was isolated by vacuum filtration, washed with water (1.5 ml), and dried in a vacuum oven at 50° C. for 20 hours to obtain 0.4 g of ibandronate sodium crystal form K2. Form K2 can exhibit a weight loss of about 9% to about 10% in TGA.

Ibandronate Sodium Form K3

Example 19

A solution of amorphous ibandronic acid (2.7 g) in water (25 ml) and sodium hydroxide (0.34 g, solid) was stirred at 70° C. The solution was poured into cold IPA (500 ml). The resulting precipitate was stirred at 0° C. for 16 hours. The precipitate was isolated by vacuum filtration and dried in a vacuum oven at 50° C. for 24 hours to obtain 2.7 g of ibandronate sodium crystal form K3. Form K3 can exhibit a weight loss of about 7% to about 8% in TGA.

Ibandronate Sodium Form Q

Example 20

Ibandronate sodium (3 g) was dissolved in water (18 ml) at room temperature. To the obtained solution, acetone (72 ml) was added in one portion to obtain a white precipitate. The slurry was stirred at room temperature for 16 hours. The precipitate was isolated by vacuum filtration, washed with acetone (2×20 ml), and dried in a vacuum oven at 50° C. for 20 hours to obtain 2.8 g of ibandronate sodium crystal form Q. Form Q can exhibit a weight loss of about 5% to about 25% in TGA.

Example 21

Ibandronate sodium (3 g) was dissolved in water (18 ml) at room temperature. To the obtained solution, acetonitrile (70 ml) was added in one portion to obtain a white precipitate. The slurry was stirred at room temperature for 16 hours. The precipitate was isolated by vacuum filtration, washed with acetonitrile (3×15 ml), and dried in a vacuum oven at 50° C. for 24 hours to obtain 2.5 g of ibandronate sodium crystal form Q.

Example 22

Ibandronate sodium (3 g) was dissolved in water (6 ml) at reflux temperature. To the obtained solution, acetone (50 ml) was added dropwise at reflux temperature to obtain a white precipitate. The slurry was stirred at reflux temperature for 4.5 hours, and then cooled to room temperature. The precipitate was isolated by vacuum filtration and washed with acetone (3×13 ml) to obtain 4.1 g of wet ibandronate sodium crystal form Q.

Example 23

A slurry of amorphous ibandronic acid (4.6 g) in acetone (96 ml) was heated to reflux temperature. Sodium hydroxide (0.58 g, solid) was added, and the reaction mixture was stirred at reflux temperature for an additional 10 hours to obtain a pH of 3.35. Then the reaction mixture was cooled to room temperature. Further cooling was performed using an ice-bath. The white solid was filtered, washed with acetone (2×25 ml), and dried in a vacuum oven at 50° C. for 21 hours to give 4.5 g of ibandronate sodium crystal form Q.

Example 24

A slurry of amorphous ibandronic acid (5 g) in ethanol (50 ml) was heated to reflux temperature. Sodium hydroxide (0.63 g, solid) was added, and the reaction mixture was stirred at reflux temperature for an additional 4 hours to obtain a pH of 3.5. Then the reaction mixture was cooled to room temperature. Further cooling was performed using an ice-bath. The white solid was filtered, washed with ethanol (2×25 ml), and dried in a vacuum oven at 50° C. for 20 hours to give 5.5 g of ibandronate sodium crystal form Q.

Example 25

A solution of amorphous ibandronic acid (4.5 g) in water (11 ml) and sodium hydroxide (0.56 g, solid) was stirred at room temperature. The solution was added dropwise into acetone (100 ml). The resulting precipitate was stirred at room temperature for 16 hours. The precipitate was isolated by vacuum filtration, washed with acetone (2×10 ml), and dried in a vacuum oven at 50° C. for 24 hours to obtain 4.8 g of ibandronate sodium crystal form Q.

Example 26

A solution of sodium hydroxide (0.63 g) in water:acetonitrile (20:80 v/v, 12.5 ml) was added dropwise to a solution of amorphous ibandronic acid (5 g) in water:acetonitrile (20:80 v/v, 50 ml) at reflux temperature. The reaction mixture was heated at reflux temperature for an additional 20 minutes to obtain a pH of 3.80. Then the reaction mixture was cooled to room temperature and stirred for 16 hrs. The precipitate was isolated by vacuum filtration, washed with acetonitrile (2×10 ml), and dried in a vacuum oven at 50° C. for 22.5 hours to obtain 4.0 g of ibandronate sodium crystal form Q.

Example 27

A solution of sodium hydroxide (0.63 g) in a mixture of water:acetonitrile (60:40 v/v, 19 ml) was added dropwise to a solution of amorphous ibandronic acid (5 g) in water:acetonitrile (60:40 v/v, 106 ml) at reflux temperature. The solution was heated at reflux temperature for an additional 1 hour. Then the reaction mixture was cooled to room temperature. Further cooling was performed using an ice-bath. Seeding was done, and the reaction mixture was stirred at 10° C. for 16 hours. The precipitate was isolated by vacuum filtration, washed with acetonitrile (2×10 ml), and dried in a vacuum oven at 50° C. for 23 hours to obtain 1.0 g of ibandronate sodium crystal form Q.

Ibandronate Sodium Form Q1

Example 28

Ibandronate sodium (3 g) was dissolved in water (18 ml) at room temperature. To the obtained solution, 2-butanol (40 ml) was added in one portion to obtain a white precipitate. The slurry was stirred at room temperature for 16 hours. The precipitate was isolated by vacuum filtration, washed with 2-butanol (2×16 ml), and dried in a vacuum oven at 50° C. for 24 hours to obtain 2.2 g of ibandronate sodium crystal form Q1. Form Q1 can exhibit a weight loss of about 9% to about 16% in TGA.

Example 29

A solution of ibandronate sodium (1 g) in water (8 ml) was dropped into tetrahydrofuran (THF) while stirring at room temperature. The slurry was stirred at room temperature for 16 hours. The precipitate was isolated by vacuum filtration and dried in a vacuum oven at 50° C. for 22.5 hours to obtain 0.98 g of ibandronate sodium crystal form Q1.

Ibandronate Sodium Form Q2

Example 30

Ibandronate sodium (3 g) was dissolved in water (6 ml) at reflux temperature. To the obtained solution, acetonitrile (50 ml) was added dropwise at reflux temperature to obtain a white precipitate. The slurry was stirred at reflux temperature for 4.5 hours. The slurry was cooled to room temperature and stirred for 16 hours. The precipitate was isolated by vacuum filtration, washed with acetonitrile (3×20 ml), and dried in a vacuum oven at 50° C. for 24 hours to obtain 3 g of ibandronate sodium crystal form Q2. Form Q2 can exhibit a weight loss of about 16% and about 17% in TGA.

Example 31

A solution of amorphous ibandronic acid (4.5 g) in water (20 ml) and 1 N aqueous sodium hydroxide (14 ml) was stirred at room temperature to obtain a pH of 3.5. The solution was added dropwise into 2-butanol (100 ml) while stirring. The obtained precipitate was stirred at room temperature for 16 hours. The precipitate was isolated by vacuum filtration, washed with 2-butanol (2×20 ml), and dried in a vacuum oven at 50° C. for 24 hours to obtain 4.4 g of ibandronate sodium crystal form Q2.

Ibandronate Sodium Form Q3

Example 32

A solution of sodium hydroxide (0.63 g) in water:methanol (60:40 v/v, 19 ml) was added dropwise to a solution of amorphous ibandronic acid (5 g) in water:methanol (60:40 v/v, 106 ml) at reflux temperature. The reaction mixture was heated at reflux temperature for an additional 1.5 hours to obtain a pH of 4.01. Then the reaction mixture was cooled to room temperature. Further cooling was performed using an ice-bath. The precipitate was filtered, washed with methanol (2×25 ml), and dried in a vacuum oven at 50° C. for 19 hours to give 5.2 g of ibandronate sodium crystal form Q3. Form Q3 can exhibit a weight loss of about 7% to about 9% in TGA.

Example 33

A slurry of amorphous ibandronic acid (5 g) in methanol (50 ml) was heated to reflux temperature. Sodium hydroxide (0.63 g, solid) was added, and the reaction mixture was stirred at reflux temperature for an additional 4 hours to obtain a pH of 4.0. Then the reaction mixture was cooled to room temperature. Further cooling was performed using an ice-bath. The white solid was filtered, washed with methanol (2×25 ml), and dried in a vacuum oven at 50° C. for 19 hours to give 4.7 g of ibandronate sodium crystal form Q3.

Ibandronate Sodium Form Q4

Example 34

A solution of amorphous ibandronic acid (4.5 g) in water (9 ml) and sodium hydroxide (0.63 g, solid) was stirred at reflux temperature. The solution was poured into a cold acetone (100 ml). The resulting precipitate was stirred at 3° C. for 2 hours. The precipitate was isolated by vacuum filtration, washed with cold acetone (2×15 ml), and dried in a vacuum oven at 50° C. for 24 hours to obtain 5.0 g of ibandronate sodium crystal form Q4. Form Q4 can exhibit a weight loss of about 7% to about 8% in TGA.

Ibandronate Sodium Form Q5

Example 35

A solution of sodium hydroxide (0.63 g) in water:acetonitrile (40:60 v/v, 12.33 ml) was added dropwise to a solution of amorphous ibandronic acid (5 g) in water:acetonitrile (40:60 v/v, 71 ml) at reflux temperature. The reaction mixture was heated at reflux temperature for an additional 1 hour to obtain a pH of 4.05. Then the reaction mixture was cooled to room temperature. Further cooling was performed using an ice-bath. The precipitate was isolated by vacuum filtration, washed with acetonitrile (2×20 ml), and dried in a vacuum oven at 50° C. for 20 hours to obtain 3.9 g of ibandronate sodium crystal form Q5. Form Q5 can exhibit a weight loss of about 5% to about 11% in TGA.

Example 36

A solution of amorphous ibandronic acid (5 g) in ethanol (50 ml) was stirred at room temperature. Aqueous sodium hydroxide (0.63 g, 12.5 ml) was added, and the reaction mixture was stirred at room temperature for an additional 2 hours. The precipitate was isolated by vacuum filtration, washed with ethanol (50 ml), and dried in a vacuum oven at 50° C. for 24 hours to obtain 5.5 g of ibandronate sodium crystal form Q5.

Example 37

A solution of amorphous ibandronic acid (5 g) in methanol (100 ml) was stirred at room temperature. Solid sodium hydroxide (0.63 g) was added. The obtained precipitate was stirred at room temperature for an additional 22 hours. The precipitate was isolated by vacuum filtration, washed with methanol (30 ml), and dried in a vacuum oven at 50° C. for 24 hours to obtain 5.4 g of ibandronate sodium crystal form Q5.

Ibandronate Sodium Form Q6

Example 38

A solution of amorphous ibandronic acid (5 g) in aqueous ethanol 96% (70 ml) was stirred at reflux temperature. Solid sodium hydroxide (0.63 g) was added. The obtained precipitate was cooled to room temperature and stirred for an additional 20 hours. The precipitate was isolated by vacuum filtration, washed with aqueous ethanol 96% (2×10 ml) and dried in a vacuum oven at 50° C. for 24 hours to obtain 6.0 g of ibandronate sodium crystal form Q6. Form Q6 can exhibit a weight loss of about 9% to about 10% in TGA.

Ibandronate Sodium Form QQ

Example 39

Ibandronate sodium (3 g) was dissolved in water (18 ml) at room temperature. To the obtained solution, THF (40 ml) was added in one portion to obtain a white precipitate. The slurry was stirred at room temperature for 16 hours. The precipitate was isolated by vacuum filtration, washed with THF (2×20 ml), and dried in a vacuum oven at 50° C. for 18 hours to obtain 2.1 g of ibandronate sodium crystal form QQ. Form QQ can exhibit a weight loss of about 5% to about 12%, or less in TGA.

Example 40

A solution of sodium hydroxide (0.57 g) in water:acetone (40:60 v/v, 11.4 ml) was added dropwise to a solution of amorphous ibandronic acid (4.5 g) in water:acetone (40:60 v/v, 64.4 ml) at reflux temperature. The reaction mixture was heated at reflux temperature for an additional 2 hours to obtain a pH of 4.5. Then the solution was cooled to room temperature. Further cooling was performed using an ice-bath. The precipitate was isolated by vacuum filtration, washed with acetone (2×15 ml), and dried in a vacuum oven at 50° C. for 21 hours to obtain 3.9 g of ibandronate sodium crystal form QQ.

Example 41

Amorphous ibandronic acid (5 g) was added to a solution of solid sodium hydroxide (0.6 g) dissolved in 93% ethanol (100 ml) at 55° C. The obtained slurry was stirred at 55° C. for 3 hours. Then the slurry was cooled to room temperature. The precipitate was isolated by vacuum filtration, washed with 93% ethanol (3×25 ml), and dried in a vacuum oven at 50° C. for 24 hours to give 4.5 g of ibandronate sodium crystal form QQ.

Example 42

A solution of ibandronate sodium (1.5 g) and water (9 ml) was stored under a saturated atmosphere of acetone (9 ml) at room temperature for 2 weeks. Then the solution was decanted, and the product was dried in a vacuum oven at 50° C. for 18 hours to give 0.9 g of ibandronate sodium crystal form QQ.

Example 43

A solution of sodium hydroxide (0.63 g) in water (12.5 ml) was added dropwise to a slurry of amorphous ibandronic acid (5 g) in ethanol (70 ml) at reflux temperature. Then the solution was cooled to room temperature and stirred for 72 hours to obtain a pH of 4.15. The precipitate was isolated by vacuum filtration, washed with ethanol (2×25 ml), and dried in a vacuum oven at 50° C. for 23 hours to obtain 4.97 g of ibandronate sodium crystal form QQ.

Example 44

A solution of sodium hydroxide (0.63 g) in ethanol (14 ml) was added dropwise to a solution of ibandronic acid (5 g) in water (50 ml) at room temperature. The obtained slurry was stirred for 3 hours to obtain a pH of 4.1. The precipitate was isolated by vacuum filtration, washed with ethanol (2×25 ml) and dried in a vacuum oven at 50° C. for 22 hours to obtain 5.4 g of ibandronate sodium crystal form QQ.

Ibandronate Sodium Form R

Example 45

Ibandronate sodium (3 g) was dissolved in water (18 ml) at room temperature. To the obtained solution, ethanol (40 ml) was added in one portion to obtain a white precipitate. The slurry was stirred at room temperature for 16 hours. The precipitate was isolated by vacuum filtration and washed with ethanol (2×20 ml) to obtain 3.3 g of wet ibandronate sodium crystal form R. Form R can exhibit a weight loss of about 10% to about 16%, or less in TGA.

Example 46

A solution of sodium hydroxide (0.63 g) in water:ethanol (60:40 v/v, 19 ml) was added dropwise to a solution of amorphous ibandronic acid (5 g) in water:ethanol (60:40 v/v, 106 ml) at reflux temperature. The reaction mixture was heated at reflux temperature for an additional 3.5 hours to obtain a pH of 4.03. Then the reaction mixture was cooled to room temperature. Further cooling was performed using an ice-bath. The precipitate was filtered, washed with ethanol (2×25 ml), and dried in a vacuum oven at 50° C. for 19 hours to give 4.7 g of ibandronate sodium crystal form R.

Example 47

A solution of sodium hydroxide (0.63 g) in water:methanol (20:80 v/v, 10 ml) was added dropwise to a solution of amorphous ibandronic acid (5 g) in water:methanol (20:80 v/v, 53 ml) at reflux temperature. The reaction mixture was heated at reflux temperature for an additional 1.5 hours to obtain a pH of 4.15. Then the reaction mixture was cooled to room temperature. Further cooling was performed using an ice-bath. The precipitate was filtered, washed with methanol (2×25 ml), and dried in a vacuum oven at 50° C. for 21 hours to give 5.2 g of ibandronate sodium crystal form R.

Example 48

A solution of sodium hydroxide (0.63 g) in water:methanol (40:60 v/v, 12 ml) was added dropwise to a solution of amorphous ibandronic acid (5 g) in water:methanol (40:60 v/v, 71 ml) at reflux temperature. The reaction mixture was heated at reflux temperature for an additional 1.5 hours to obtain a pH of 4.04. Then the reaction mixture was cooled to room temperature. Further cooling was performed using an ice-bath. The precipitate was filtered, washed with methanol (2×25 ml), and dried in a vacuum oven at 50° C. for 21 hours to give 5.1 g of ibandronate sodium crystal form R.

Example 49

Sodium hydroxide (0.63 g, solid) was added to a solution of amorphous ibandronic acid (5 g) in water:ethanol (60:40 v/v, 125 ml) at reflux temperature. The reaction mixture was heated at reflux temperature for an additional 25 minutes. Then the reaction mixture was cooled to room temperature to obtain a precipitate (pH=4.10). Further cooling was performed using an ice-bath. The precipitate was filtered, washed with ethanol (2×25 ml), and dried in a vacuum oven at 50° C. for 21 hours to give 5.2 g of ibandronate sodium crystal form R.

Example 50

A solution of sodium hydroxide (0.63 g) in water:ethanol (60:40 v/v, 19 ml) was added dropwise to a solution of amorphous ibandronic acid (5 g) in water:ethanol (60:40 v/v, 106 ml) at room temperature. The reaction mixture was stirred at room temperature for an additional 16 hours to obtain a pH of 4.11. The white solid was filtered, washed with ethanol (2×25 ml), and dried in a vacuum oven at 50° C. for 21 hours to give 5.1 g of ibandronate sodium crystal form R.

Ibandronate Sodium Form S

Example 51

A solution of sodium hydroxide (0.63 g) in water:ethanol (40:60 v/v, 12 ml) was added dropwise to a solution of amorphous ibandronic acid (5 g) in water:ethanol (40:60 v/v, 71 ml) at reflux temperature. The reaction mixture was heated at reflux temperature for an additional 3.5 hours to obtain a pH of 4.03. Then the reaction mixture was cooled to room temperature. Further cooling was performed using an ice-bath. The precipitate was filtered, washed with ethanol (2×25 ml), and dried in a vacuum oven at 50° C. for 18 hours to give 4.9 g of ibandronate sodium crystal form S. Form S can exhibit a weight loss of about 11% to about 12%, or less in TGA.

Ibandronate Sodium Form T

Example 52

A solution of sodium hydroxide (0.58 g) in water:acetone (20:80 v/v, 9 ml) was added dropwise to a solution of amorphous ibandronic acid (5 g) in water:acetone (20:80 v/v, 49 ml) at reflux temperature. The reaction mixture was heated at reflux temperature for an additional 1.5 hours to obtain a pH of 4.0. Then the reaction mixture was cooled to room temperature. Further cooling was performed using an ice-bath. The precipitate was filtered, washed with acetone (1×50 ml), and dried in a vacuum oven at 50° C. for 21 hours to give 3.8 g of ibandronate sodium crystal form T. Form T can exhibit a weight loss of about 5% and about 7% in TGA.

Amorphous Ibandronate Sodium

Example 53

Ibandronate sodium (3 g) was dissolved in DMSO (10 ml) at 120° C. To the obtained solution, acetone (40 ml) was added dropwise to obtain a white precipitate. The slurry was stirred at reflux for 3.5 hours. The solution was cooled to room temperature and stirred for 16 hours. The gelatinous precipitate was isolated by vacuum filtration and dried in a vacuum oven at 50° C. for 24 hours to obtain 2.7 g of amorphous ibandronate sodium. The amorphous ibandronate sodium can exhibit a weight loss of about 6.8% to about 24.4%, or less in TGA.

Example 54

Ibandronate sodium (3 g) was dissolved in DMSO (10 ml) at 120° C. To the obtained solution, acetone (40 ml) was added dropwise to obtain a white precipitate. The slurry was stirred at reflux for 10 minutes. The solution was cooled to room temperature and stirred for 16 hours. The gelatinous precipitate was isolated by vacuum filtration and dried in a vacuum oven at 50° C. for 24 hours to obtain 2.2 g of amorphous ibandronate sodium.

Example 55

A solution of sodium hydroxide (0.63 g) in water:ethanol (80:20 v/v, 38 ml) was added dropwise to a solution of amorphous ibandronic acid (5 g) in water:ethanol (80:20 v/v, 212 ml) at reflux temperature. The reaction mixture was heated at reflux temperature for an additional 3 hours to obtain a pH of 3.24. Then the reaction mixture was cooled to room temperature. The clear solution was evaporated until dry to obtain 5.7 g of amorphous ibandronate sodium.

Example 56

A solution of sodium hydroxide (0.63 g) in water:IPA (80:20 v/v, 38 ml) was added dropwise to a solution of amorphous ibandronic acid (5 g) in water:IPA (80:20 v/v, 212 ml) at reflux temperature. The reaction mixture was heated at reflux temperature for an additional 45 minutes. Then the reaction mixture was cooled to room temperature. The clear solution was evaporated until dry to give 5.9 g of amorphous ibandronate sodium.

Example 57

A slurry of amorphous ibandronic acid (5 g) in acetonitrile (50 ml) was heated to reflux temperature. Solid sodium hydroxide (0.63 g) was added. The reaction mixture was stirred at reflux temperature for an additional 6 hours. Then the reaction mixture was cooled to room temperature. Further cooling was performed using an ice-bath to obtain clear gel (pH=4.05). The gelatinous product was dried in a vacuum oven at 50° C. for 24 hours to give 2.6 g of amorphous ibandronate sodium.

Example 58

A solution of sodium hydroxide (0.63 g) in water:acetonitrile (60:40 v/v, 19 ml) was added dropwise to a solution of amorphous ibandronic acid (5 g) in water:acetonitrile (60:40 v/v, 106 ml) at reflux temperature. The reaction mixture was heated at reflux temperature for an additional 1 hour. Then the reaction mixture was cooled to room temperature. Further cooling was performed using an ice-bath. The clear solution was seeded with ibandronate sodium form K1, and stirred for 16 hours. The mother liquid was evaporated until dry to give 3.5 g of amorphous ibandronate sodium.

Example 59

A solution of sodium hydroxide (0.55 g) in water:acetonitrile (80:20 v/v, 33 ml) was added dropwise to a solution of amorphous ibandronic acid (4 g) in water:acetonitrile (80:20 v/v, 187 ml) at reflux temperature. Then the reaction mixture was cooled to room temperature. The clear solution was evaporated until dry to obtain 5.2 g of amorphous ibandronate sodium.

Example 60

A solution of amorphous ibandronic acid (5 g) in water (50 ml) was heated to reflux temperature. Solid sodium hydroxide (0.63 g) was added, and the reaction mixture was stirred at reflux temperature for an additional 1 hour. Then the reaction mixture was cooled to room temperature. The clear solution was evaporated to give 5.6 g of amorphous ibandronate sodium.

Example 61

A slurry of amorphous ibandronic acid (5 g) in acetonitrile (50 ml) was stirred at room temperature. Solid sodium hydroxide (0.63 g) was added, and the reaction mixture was stirred at room temperature for an additional 72 hours. The precipitate was isolated by vacuum filtration and dried in a vacuum oven at 50° C. for 20 hours to obtain 5.0 g of amorphous ibandronate sodium.

Example 62

A slurry of amorphous ibandronic acid (5 g) in acetonitrile (200 ml) was stirred at reflux temperature. Solid sodium hydroxide (0.63 g) was added, and the reaction mixture was stirred at reflux temperature for an additional 2 hours. Acetone (50 ml) was added dropwise. Then the reaction mixture was cooled to room temperature and stirred for 16 hours. The precipitate was isolated by vacuum filtration, washed with acetone (50 ml), and dried in a vacuum oven at 50° C. for 22 hours to obtain 3.5 g of amorphous ibandronate sodium.

Example 63

A solution of amorphous ibandronic acid (5 g) in water (30 ml) was stirred at room temperature. Aqueous sodium hydroxide (0.63 g NaOH in 20 mL water) was added, and the reaction mixture was stirred at room temperature for an additional 1 hour. The solution was evaporated until dry. Hexanes (100 ml) were added to the residue and stirred for 16 hours at room temperature. The precipitate was isolated by vacuum filtration, washed with hexanes (1×50 ml), and dried in a vacuum oven at 50° C. for 45 hours to obtain 5.1 g of amorphous ibandronate sodium.

Example 64

Ibandronate sodium (9 g) was dissolved in water (90 ml) at room temperature. The solution was divided into three portions, and each portion was spray dried using a Buchi mini spray dryer B-290 using a standard nozzle 0.7 mm in diameter with a nozzle cap of 1.4 or 1.5 mm. In each instance, amorphous ibandronate sodium was obtained.

For portion 1, nitrogen gas was at an inlet temperature of 50° C. The evaporated solvent and nitrogen left the spray dryer at a temperature of 41-34° C.

For portion 2, nitrogen gas was at an inlet temperature of 100° C. The evaporated solvent and nitrogen left the spray dryer at a temperature of 77-62° C.

For portion 3, nitrogen gas was at an inlet temperature of 150° C. The evaporated solvent and nitrogen left the spray dryer at a temperature of 96-109° C.

TABLE 2

Preparation of ibandronate monosodium salt:

| | EtOH | MeOH | IPA | ACN | Acetone |
|---|---|---|---|---|---|
| 0% v/v H$_2$O | Q | Q3 | K | Amorphous | Q |
| 20% v/v H$_2$O | R + Q | R | F | Q | T |
| 40% v/v H$_2$O | S | R | F | Q5 | QQ |
| 60% v/v H$_2$O | R | Q3 | F | Q | — |
| 80% v/v H$_2$O | Amorphous | Amorphous + T | Amorphous | Amorphous | Amorphous > T |

Using amorphous IBD-Ac as a starting material

Amorphous Ibandronic Acid

Example 65

An aqueous solution (40% w/w) of ibandronic acid (150 ml) was evaporated under vacuum (20-30 mmHg) until dry while heating the flask in a water bath (up to 70° C.) to obtain amorphous ibandronic acid (67 g).

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Polymorphism in Pharmaceutical Solids, Drugs and the Pharmaceutical Sciences, Volume 95 can be used for guidance. All references mentioned herein are incorporated in their entirety.

What is claimed is:

1. A crystalline form of ibandronate sodium selected from the group consisting of:
   g) the crystalline form of ibandronate sodium characterized by x-ray reflections at about 4.6, 9.2, 18.3, 19.6, and 25.6±0.2° 2θ;
   r) the crystalline form of ibandronate sodium characterized by x-ray reflections at about 6.2, 25.9, 26.7, 31.1, and 37.2±0.2° 2θ; and
   u) the crystalline form of ibandronate sodium characterized by x-ray reflections at about 6.2, 15.7, 26.3, 32.6, and 35.6 ±0.2° 2θ.

2. The crystalline form of ibandronate sodium of claim 1, characterized by x-ray reflections at about 4.6, 9.2, 18.3, 19.6, and 25.6±0.2° 2θ, denominated Form J, and further characterized by x-ray reflections at about 17.5, 18.9, 21.7, 22.9, and 29.5±0.2° 2θ.

3. The crystalline form of ibandronate sodium of claim 2 having a powder x-ray diffraction diagram substantially as shown in FIG. 7.

4. The crystalline form of ibandronate sodium of claim 1, characterized by x-ray reflections at about 6.2, 25.9, 26.7, 31.1, and 37.2±0.2° 2θ, denominated Form QQ, and further characterized by x-ray reflections at about 16.9, 17.3, 21.5, 24.7, and 29.2±0.2° 2θ.

5. The crystalline form of ibandronate sodium of claim 4 having a powder x-ray diffraction diagram substantially as shown in FIG. 18.

6. The crystalline form of ibandronate sodium of claim 4 having a particle size distribution of not more than 100μ.

7. The crystalline form of ibandronate sodium of claim 6 having a particle size distribution of not more than 60μ.

8. The crystalline form of ibandronate sodium of claim 1, characterized by x-ray reflections at about 6.2, 15.7, 26.3, 32.6, and 35.6±0.2° 2θ, denominated Form T, and further characterized by x-ray reflections at about 17.6, 19.4, 26.9, 31.7, and 38.7±0.20° 2θ.

9. The crystalline form of ibandronate sodium of claim 8 having a powder x-ray diffraction diagram substantially as shown in FIG. 21.

* * * * *